(12) United States Patent
Fischer

(10) Patent No.: US 7,040,893 B2
(45) Date of Patent: May 9, 2006

(54) FIBER-COVERED DENTAL DELIVERY INSTRUMENTS

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 177 days.

(21) Appl. No.: 10/068,788

(22) Filed: Feb. 5, 2002

(65) Prior Publication Data

US 2002/0090591 A1    Jul. 11, 2002

Related U.S. Application Data

(63) Continuation-in-part of application No. 09/703,248, filed on Oct. 30, 2000, now Pat. No. 6,382,972, and a continuation-in-part of application No. 09/766,708, filed on Jan. 22, 2001, now Pat. No. 6,343,929.

(51) Int. Cl.
*A61C 17/00* (2006.01)

(52) U.S. Cl. .................................................. 433/80
(58) Field of Classification Search .................. 433/90, 433/89, 80, 81, 224; 401/129, 271; 15/167.1; 604/2, 310, 311
See application file for complete search history.

(56) References Cited

U.S. PATENT DOCUMENTS

| | | | |
|---|---|---|---|
| 767,469 A | 8/1904 | Ziegler | |
| 3,417,762 A | 12/1968 | Hall | |
| 3,499,686 A | 3/1970 | Landen et al. | |
| 4,199,270 A | 4/1980 | Tomasini | |
| 4,211,247 A | 7/1980 | Morganroth | |
| 4,256,409 A | 3/1981 | Manley | |
| 4,578,055 A | 3/1986 | Fischer | |
| 4,672,953 A | 6/1987 | DiVito | |
| 4,718,889 A | 1/1988 | Blasius, Jr. et al. | |
| 4,767,398 A | 8/1988 | Blasius, Jr. | |
| 4,808,022 A | 2/1989 | Iizuka et al. | |
| 4,863,380 A | 9/1989 | Creed | 433/89 |
| 4,922,936 A * | 5/1990 | Buzzi et al. | 132/321 |
| 4,941,873 A | 7/1990 | Fischer | |
| 4,963,046 A | 10/1990 | Eguchi | |

(Continued)

FOREIGN PATENT DOCUMENTS

DE     3 436 472     4/1986

(Continued)

OTHER PUBLICATIONS

Borowski, Bob, "Get a Feel for Flocking," pp. 1–4, Reprinted from *Screen Printing*, Mar. 1998.

(Continued)

*Primary Examiner*—Melba N. Bumgarner
(74) *Attorney, Agent, or Firm*—Workman Nydegger

(57) ABSTRACT

A dental delivery tool sized and configured to deliver a dental composition into a dental preparation includes: (A) a hollow body configured to deliver a dental composition therefrom; and (B) a plurality of fibers coupled to at least a portion of the hollow body. A portion of the fibers extend a length "L" distally beyond the rim of the hollow body. A portion of the fibers are coupled along the wall a distance "D" proximally with respect to the rim. The distance "D" is at least about two and one half times greater than the length "L". Employing the tool, which may be a delivery tip, for example, the interior walls of a dental preparation may be conveniently brushed or cleaned during a procedure in which a dental composition is delivered using the dental delivery tool.

40 Claims, 20 Drawing Sheets

U.S. PATENT DOCUMENTS

| | | |
|---|---|---|
| 4,997,371 A | 3/1991 | Fischer |
| 5,154,523 A | 10/1992 | Devreeze |
| 5,236,358 A | 8/1993 | Sieffert .............. 433/119 |
| 5,246,371 A | 9/1993 | Fischer |
| 5,269,684 A | 12/1993 | Fischer |
| 5,337,436 A | 8/1994 | Saxer et al. ............ 15/104.94 |
| 5,378,149 A | 1/1995 | Stropko .............. 433/80 |
| 5,693,360 A | 12/1997 | Stern et al. ............ 427/2.29 |
| 5,755,572 A | 5/1998 | Bab et al. |
| 5,800,367 A | 9/1998 | Saxer et al. ............ 601/164 |
| 5,816,804 A | 10/1998 | Fischer .............. 433/90 |
| 5,829,976 A | 11/1998 | Green .............. 433/89 |
| 5,899,693 A | 5/1999 | Himeno et al. ............ 433/119 |
| 5,908,257 A | 6/1999 | Martin .............. 401/271 |
| 5,944,519 A | 8/1999 | Griffiths .............. 433/80 |
| 6,049,934 A | 4/2000 | Discko .............. 15/106 |
| 6,059,570 A | 5/2000 | Dragan et al. ............ 433/80 |
| 6,082,999 A | 7/2000 | Tcherny et al. ............ 433/80 |
| 6,083,002 A | 7/2000 | Martin et al. ............ 433/90 |
| 6,096,382 A | 8/2000 | Gueret .............. 427/463 |
| 6,162,202 A | 12/2000 | Sicurelli et al. |
| 6,179,617 B1 | 1/2001 | Ruddle .............. 433/224 |
| 6,238,120 B1 | 5/2001 | Mark .............. 401/265 |
| 6,343,929 B1 | 2/2002 | Fischer |
| 6,382,972 B1 | 5/2002 | Fischer et al. |
| 2002/0172922 A1 | 11/2002 | Mannschedel |

FOREIGN PATENT DOCUMENTS

| | | |
|---|---|---|
| DE | 39 37 030 A1 | 5/1990 |
| DE | 39 37 030 C2 | 5/1990 |
| EP | 0 582 361 B1 | 5/1997 |
| EP | 1 147 746 | 10/2001 |
| EP | 1 258 227 | 11/2002 |
| FR | 2 288 495 | 6/1976 |
| GB | 2 225 957 | 6/1990 |
| WO | WO 89/12428 | 12/1989 |
| WO | WO 02/053053 | 7/2002 |

OTHER PUBLICATIONS

Maag, Ulrich, "Principles of Flocking," pp. 1-6, Reprinted from *Adhesives Age*, Sep. 1975, vol. 18, No. 9.

Advertisement: "*Microbrush Disposable Applicators—New & Improved for '95*", 2 pgs.

Various Internet Documents for Microbrush Corporation, http://www.microbrush.com; Jan. 9, 2003, 56 pages.

Microbrush Product, "*Flowthru*", Available on information and belief in 2001, 3 pgs.

\* cited by examiner

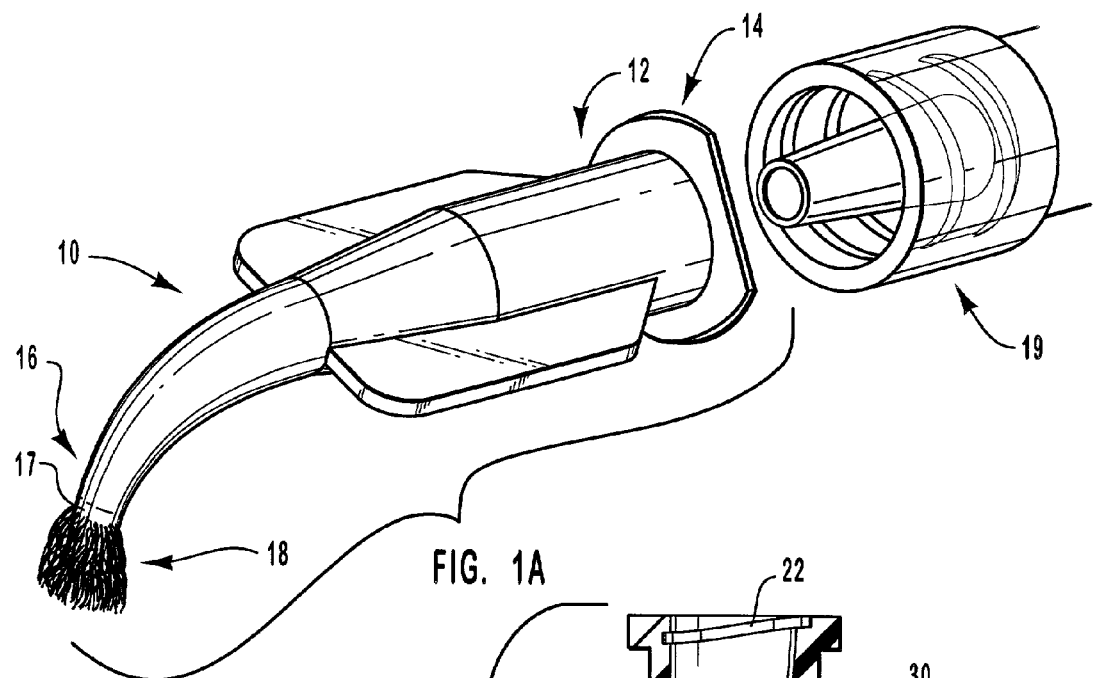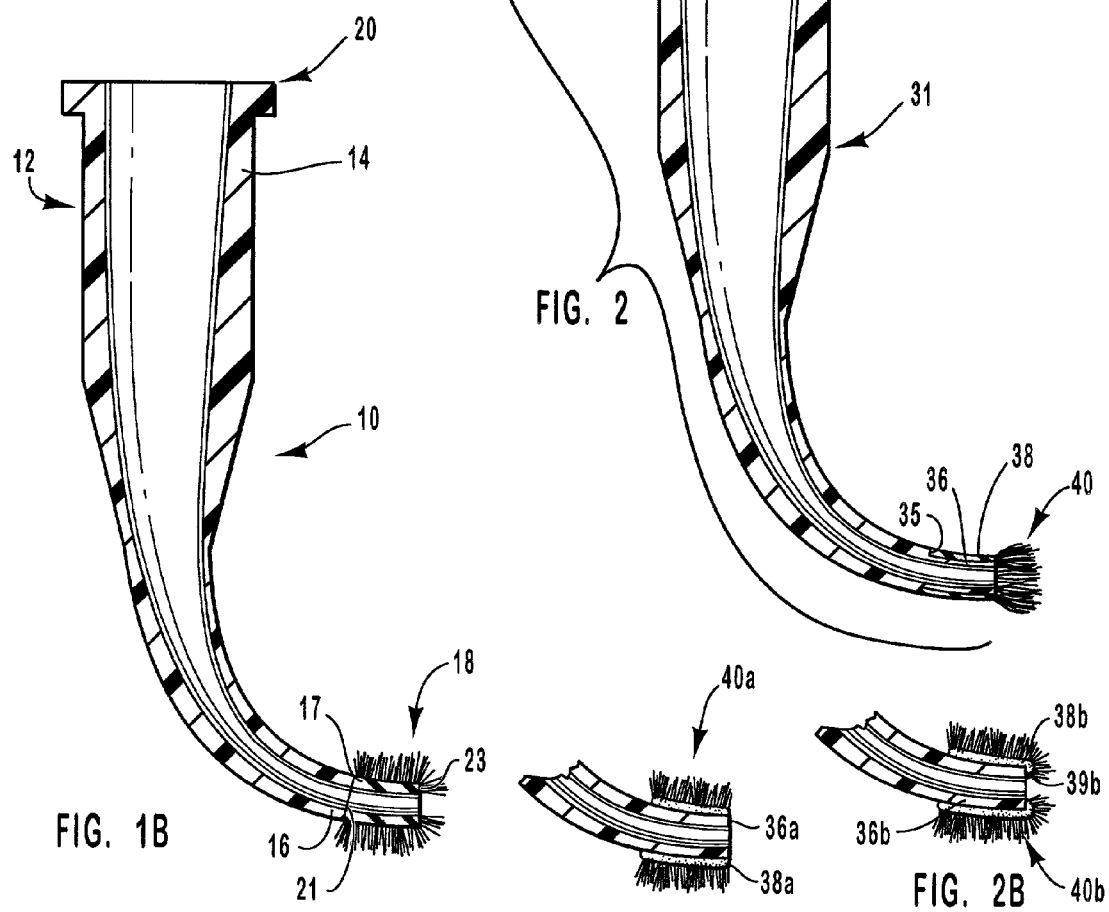
FIG. 1A
FIG. 2
FIG. 1B
FIG. 2A
FIG. 2B

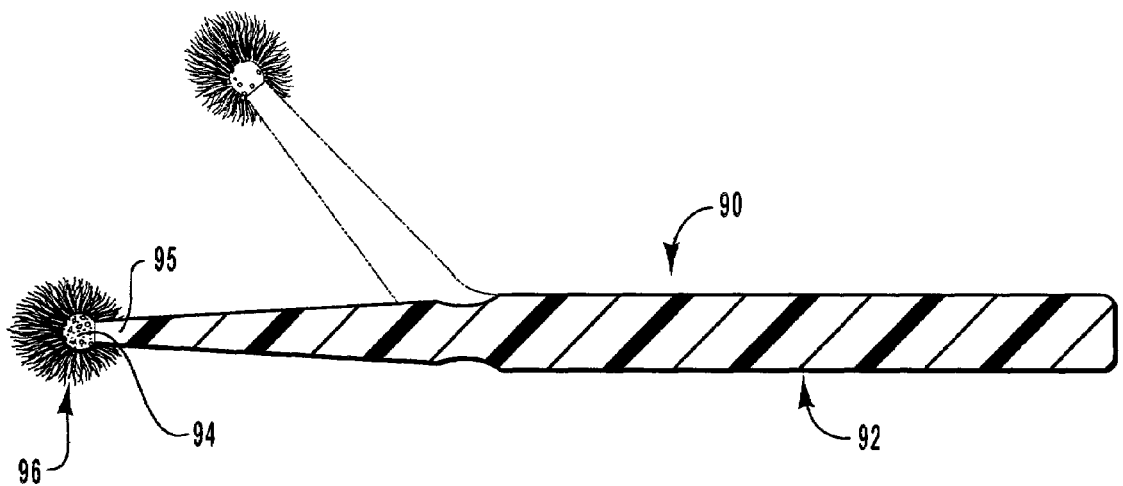
FIG. 6A
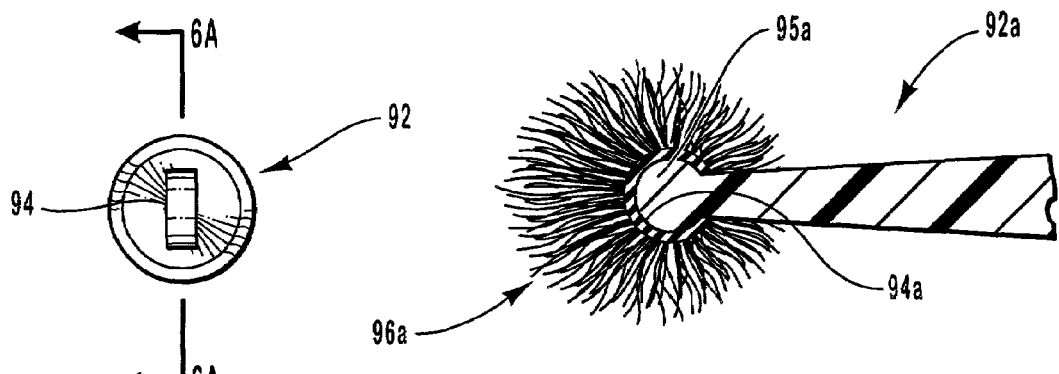
FIG. 6B
FIG. 7A
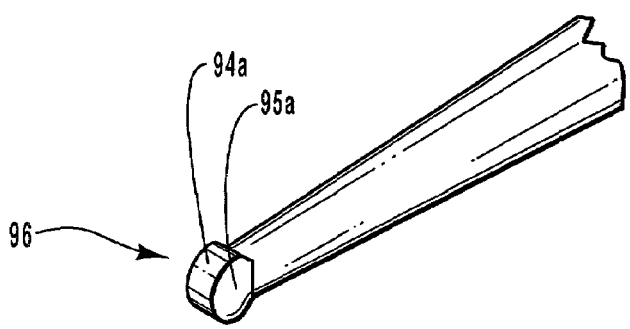
FIG. 7B

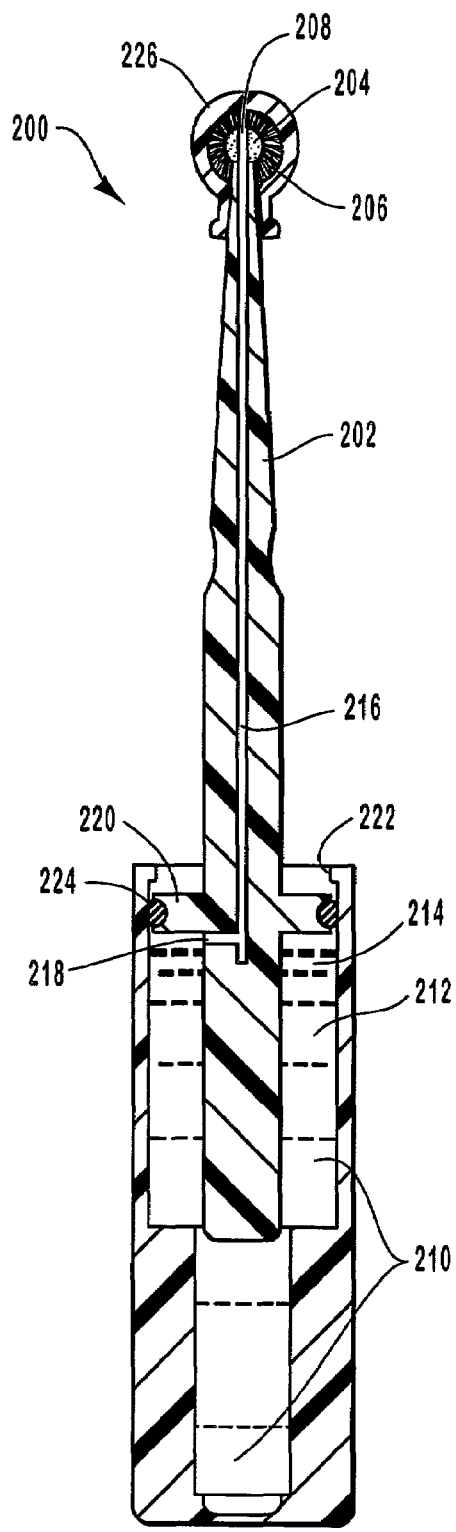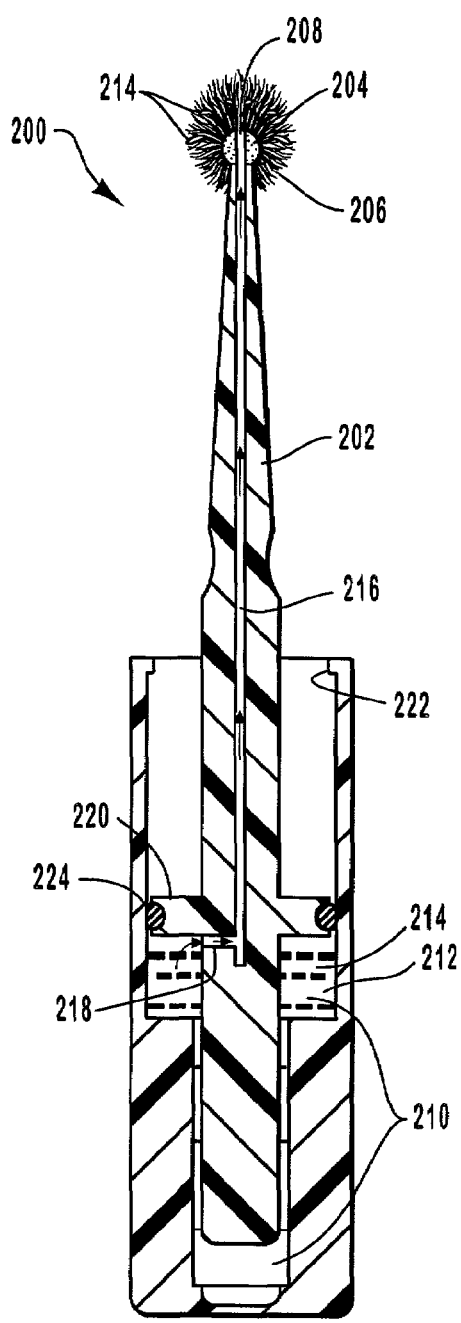
FIG. 9A
FIG. 9B

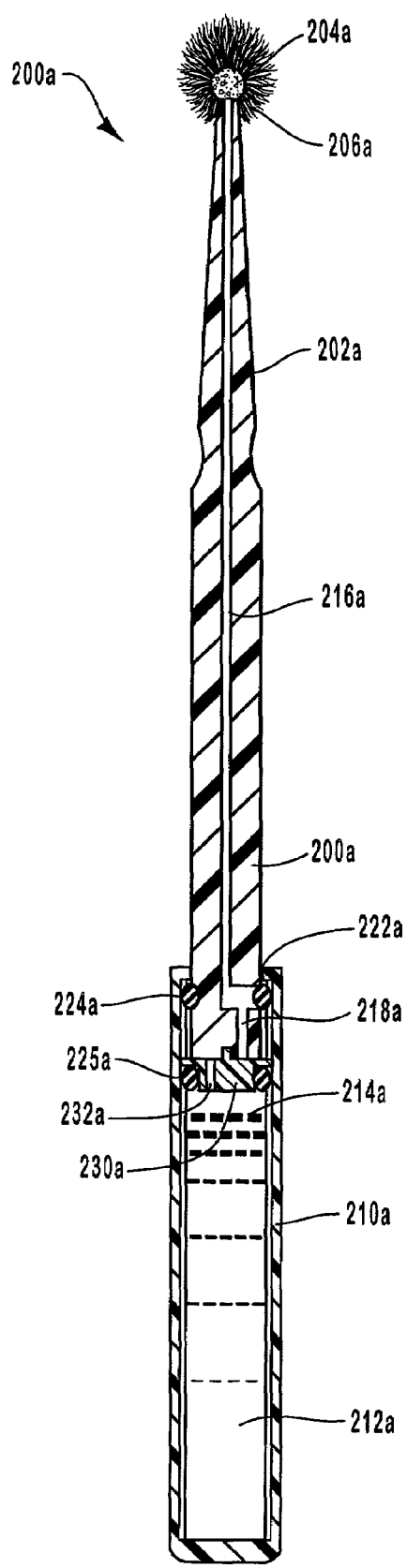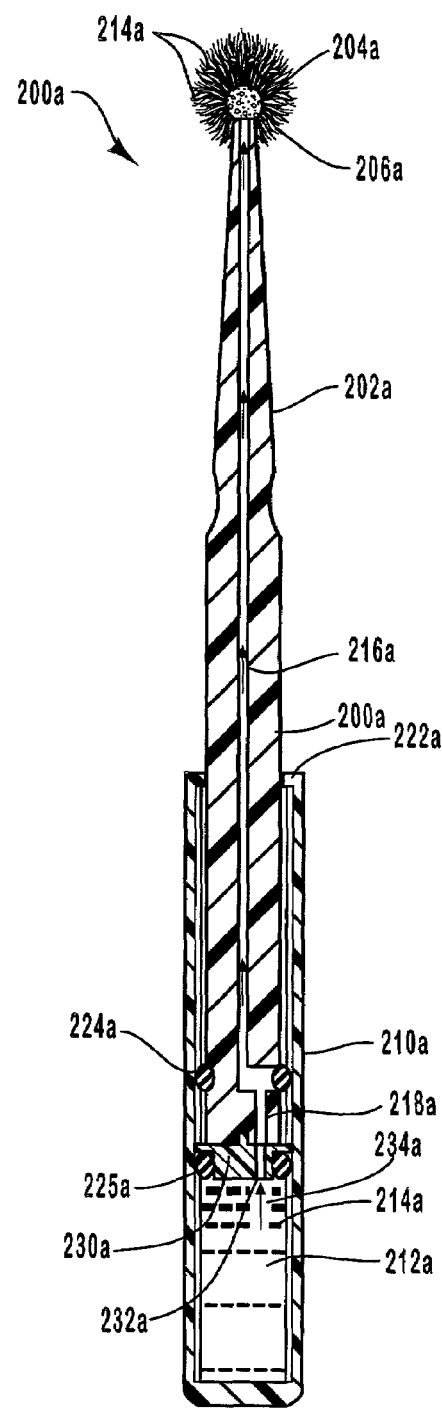
FIG. 10A
FIG. 10B

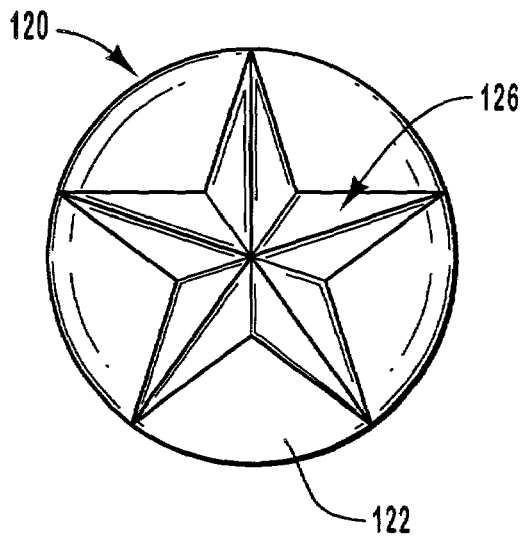
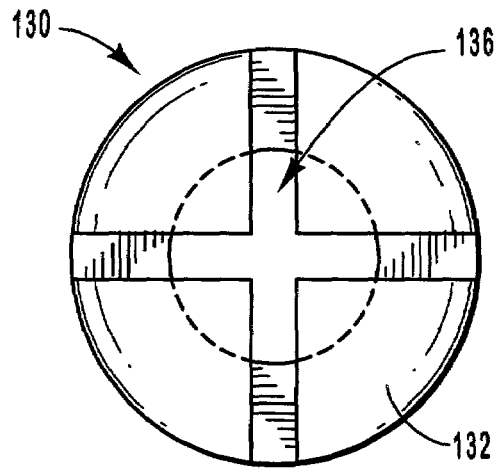
FIG. 12A
FIG. 13A
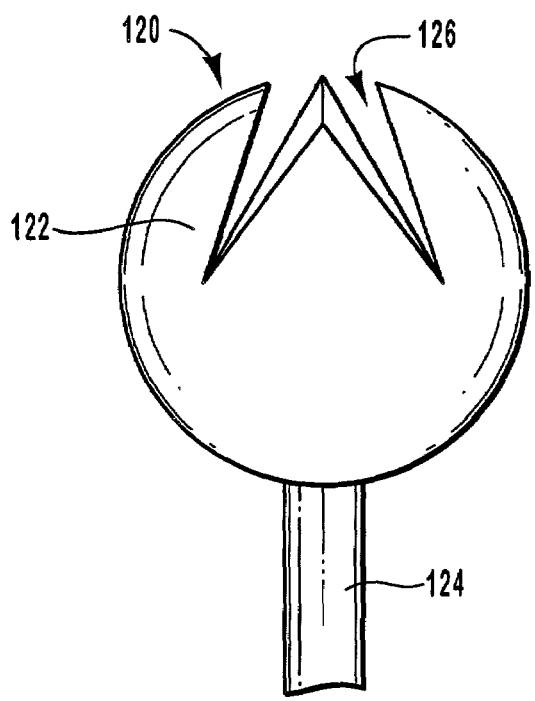
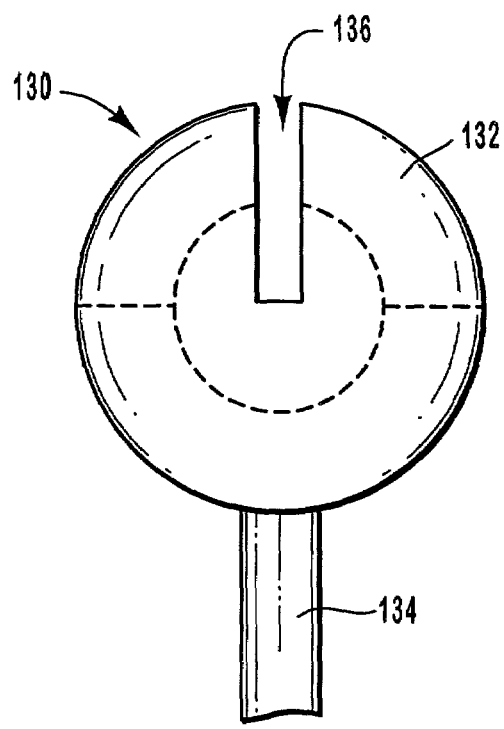
FIG. 12B
FIG. 13B

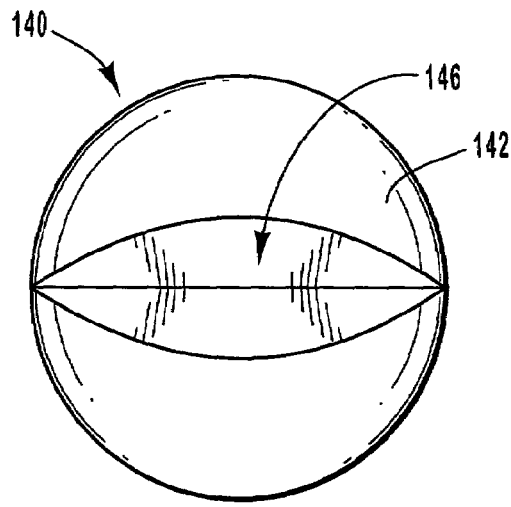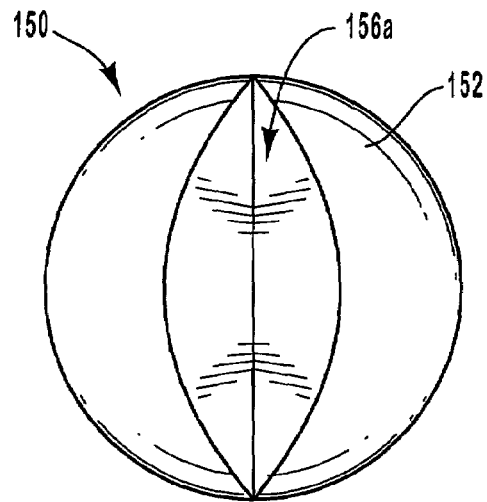
FIG. 14A  FIG. 15A
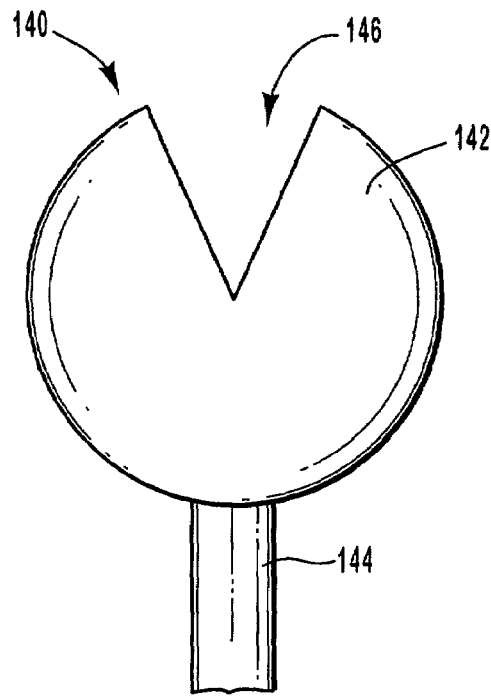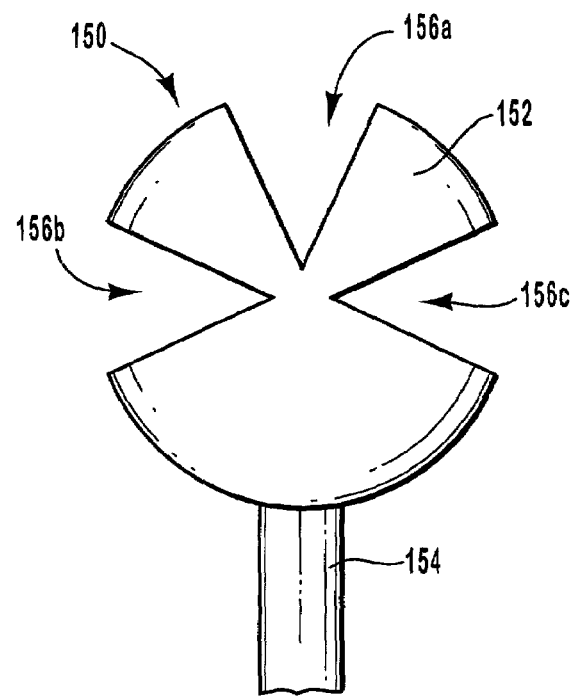
FIG. 14B  FIG. 15B

FIBER-COVERED DENTAL DELIVERY INSTRUMENTS

CONTINUITY DATA

This patent application is a continuation in part of U.S. patent application Ser. No. 09/703,248, filed Oct. 30, 2000 now U.S. Pat. No. 6,382,972 and entitled "Cushioned, Fiber-Covered Dental Delivery Tips;" and U.S. patent application Ser. No. 09/766,708, filed Jan. 22, 2001 now U.S. Pat. No. 6,343,929, and entitled "Endodontic Irrigator Tips Having Fiber Covered Cannulas and Related Methods." For purposes of disclosure, each of the foregoing patent applications are incorporated herein by reference.

BACKGROUND OF THE INVENTION

1. The Field of the Invention

The present invention relates to dental delivery tools and components thereof for use in dentistry and medicine and other fields. More particularly, the present invention is directed to dental delivery instruments configured for insertion into the mouth of a patient and having a plurality of fibers disposed along a desired length of the delivery end portion.

2. The Relevant Technology

There are many important dental compositions that need to be efficiently delivered to tooth surfaces during dental restorative procedures. Such dental compositions include, for example, hemostatic agents, etchants, bonding agents, disinfectants, sealants, and for indirect impression making, impression materials. Applicators and syringes with associated delivery tips are often employed to deposit such compositions onto the teeth and gums of a patient. Dental instruments are also sometimes employed adjacent teeth and gums without depositing a composition thereon, such as when probing, cleaning, or examining a tooth or gum.

Since dental instruments such as syringes and applicators are moved in such close proximity near teeth and gums of a patient, and sometimes even contact the teeth and gums of a patient, typical dental instruments can cause pain and irritation to the teeth and gums of the patient, particularly when the patient has injured or bleeding gums, or sensitive teeth, for example.

For instance, it is typical for practitioners to move a dental instrument adjacent the teeth and gums of a patient when the practitioner is removing air bubbles from dental compositions, such as impression materials, applied to the teeth and/or gums of a patient. Impression materials are applied to the teeth and allowed to harden to thereby make an impression of the teeth. The hardened impression materials are then used to make a mold.

When applying impression materials to a tooth, air bubbles can remain entrapped within the impression material, particularly when a syringe is used in dispensing the impression material. These air bubbles can prevent complete reproduction of detail in the impression material, resulting in a poor cast mold of the teeth.

The impression material is only useable for a few minutes once the base material and the catalyst material have been mixed. Thus, it is important to remove entrapped air bubbles as soon as possible. In conventional delivery methods, after a quantity of impression material has been delivered around the prepared tooth, an air syringe is sometimes used to blow against the impression material. This can help to break up entrapped bubbles, but is not always predictable and can result in additional air bubbles becoming entrapped in the impression material. In addition, time is wasted addressing this issue while working time of the impression material is passing.

Although bristled dental instruments are highly useful for a variety of different purposes, such as removing air bubbles, one drawback relating to typical bristled instruments is that the instruments can contact and irritate sensitive root, nerve, and gum tissues. During use of bristled dental instruments, the instruments must necessarily be moved adjacent root, nerve, and gum tissues. In order to be effective, the instruments must be moved close enough to the teeth and gums that the bristles can be brushed against a composition placed on the teeth and gums.

Despite the greatest care exercised by the dentist, it is generally very difficult, if not impossible for the dentist to move a dental instrument adjacent the teeth and gums of a patient without, on occasion, accidentally abutting an end of the instrument against the teeth and gums. The contact of the instrument against the teeth and gums can be particularly painful in the event of an abscess, injury, sensitive gums, missing teeth, and other conditions potentially causing pain upon contact with a dental instrument.

Another challenge within the art relates to the movement of dental instruments into spaces between teeth and into or adjacent crevices and tight spaces within teeth, such as during delivery of dental materials therein. This challenge is increased when sensitive teeth and gums are involved.

What is therefore needed is a dental instrument and a method for using the dental instrument in a manner that does not injure the teeth and gums of a patient when the dental instrument contacts the teeth and gums. What is also needed is a dental instrument having at least some degree of fibrous covering without causing injury or pain in the event of contact between a dental instrument and the teeth or gums of a patient. What is also needed is a dental instrument that is readily placed into spaces between teeth and into or adjacent crevices and tight spaces within teeth, such as during delivery of dental materials therein or during a cleaning procedure.

Another challenge within the art that relates to the delivery of dental compositions relates to the difficulty of accessing the sides of a dental surface, such as the interior surfaces of a cavity formed within the tooth of a patient. While it may be possible to deliver a dental composition to the top or bottom of a cavity or root canal from a delivery tip, it is often difficult to spread the composition on the interior walls of a cavity formed in the mouth without having to carefully manipulate the dispensing device. What is therefore also needed is a dental delivery instrument with which it is convenient to deliver a composition to the walls of a dental surface, such as the interior walls of a cavity or root canal.

SUMMARY AND OBJECTS OF THE INVENTION

It is therefore an object of the invention to provide an improved dental instrument.

It is another object of the invention to provide an improved dental instrument that does not injure the teeth and gums of a patient contacted by the dental instrument.

It is another object of the invention to provide a cushioned dental delivery instrument and methods for the use thereof.

It is another object of the invention to provide a dental delivery instrument capable of conveniently moving into spaces between teeth and into and adjacent crevices and tight spaces within teeth.

It is another object of the invention to provide an improved dental instrument having a plurality of fibers thereon.

It is another object of the invention to provide a dental instrument having a main body that is selectively placed adjacent the teeth and gums of a patient without injuring or causing pain to the teeth or gums.

It is another object of the invention to provide an improved delivery tip for delivering a dental composition to a desired location.

It is another object of the invention to provide an improved dental applicator.

It is another object of the invention to provide a fibrous dental instrument that a dental practitioner can employ without injuring or causing pain to teeth and gums.

It is another object of the invention to provide a dental instrument that can be conveniently used as a dental cleaning instrument.

It is another object of the invention to provide a dental instrument that conforms to crevices and tight places within teeth and other portions of the mouth of a patient.

It is another object of the invention to provide a dental delivery instrument with which it is convenient to deliver a composition to the interior walls of a cavity or root canal.

It is another object of the invention to provide a dental delivery instrument with which it is convenient to deliver a composition to the exterior of a dental surface, such as a tooth or the gums of a patient.

It is another object of the invention to provide a dental delivery instrument with which it is convenient to brush a dental surface, including the walls of a dental preparation, such as a cavity or root canal.

In one aspect, this invention relates to the mounting of an elastomeric member on the main body of a dental instrument in order to conform to difficult tooth surfaces and/or prevent injury or pain upon the movement of the instrument against the teeth or gums of a dental patient. The main body, typically an elongate rigid body, and the elastomeric member form a cushioned dental instrument.

The cushioned dental instrument of the present invention may comprise, for example, a fiber-covered, cushioned instrument such as a delivery tip that is selectively coupled to a syringe. Optionally, the cushioned dental instrument may comprise a fiber-covered, cushioned dental applicator. As the practitioner moves the cushioned portion of the instrument close to the teeth and gums in order to apply or brush a dental composition, for example, the elastomeric member cushions any contact of the instrument against the teeth or gums.

One such cushioned dental instrument comprises: (i) a rigid, elongate, main body configured to be grasped by a practitioner; (ii) an elastomeric member coupled to the main body; and (iii) a plurality of flocking fibers electrostatically deposited on the elastomeric member. The fibers are affixed at an adhesion end thereof to the elastomeric member. The opposing free ends of the flocking fibers extend away from the elastomeric member. The fibers of the dental tool permit an agitating action to remove air bubbles from the applied dental composition such as an impression material, reducing the amount of air entrapped within the impression material. The stimulation provided by the fibers also results in better adaptation of the applied material around tooth surfaces. The fibers may also be used in a brushing or scrubbing action, which is advantageous for working other dental compositions into the tissues.

As indicated, examples of the dental instrument include an applicator and a delivery tip. The cushioned member of a particular instrument may have a variety of different configurations, such as square, round, or a variety of different shapes. Grooves can be located in the cushioned member to enable the cushioned member to contract when it is placed between or adjacent teeth. Such grooves may have a variety of different configurations.

The dental tools of the present invention may be formed through the use of two or three color molding (or optionally, four, five or six color molding, for example, if many different materials are employed), adhesion, ultrasonic bonding, or through a variety of different techniques in which an elastomeric member is coupled to a rigid material.

A delivery tip of the present invention may be used to apply a dental composition to a tooth surface. One delivery tip comprises a tubular member, means for coupling the tubular member to a delivery device, an elastomeric member coupled to the tubular member, and a plurality of fibers coupled to the elastomeric member. An applicator of the present invention comprises a main body, an elastomeric member coupled to the main body, and a plurality of fibers coupled to the elastomeric member.

The body of the dental tool of the present invention, such as a delivery tip or applicator, may comprise a solid, rigid polypropylene, while the elastomeric portion may comprise a soft, elastomeric member, such as a thermoplastic elastomer, or a urethane, for example. Preferably, the dental instrument is made from a chemically inert material with respect to the dental compositions. The durometer of the elastomeric member may vary based on the durometer of the material to be delivered, with higher durometer elastomeric members being employed for higher durometer materials to be delivered, for example.

A handle of the dental tool may be formed through the use of a rigid material combined with an elastomeric member, thereby forming a non-slip grip, such as on the applicators of the present invention. Such a handle may be formed through two or three color molding, for example, and through the use of a number of different materials.

One delivery system of the present invention comprises a cushioned dental instrument and a delivery device coupled to the cushioned dental instrument. For example, a fiber-covered, cushioned delivery tip may be coupled to a syringe that has a reservoir and a plunger that selectively forces material from the reservoir. In another embodiment of a delivery system, an applicator system comprises a hollow main body and a reservoir movably coupled thereto. Upon movement of the applicator's main body with respect to the reservoir, a desired amount of material is delivered from the hollow main body.

Another major advantage of a cushioned dental instrument of the present invention is the ability of the cushioned instrument (with or without fibers) to accommodate irregularities in tooth and gum surfaces while still performing the delivery function desired. For example, a cushioned applicator is able to readily negotiate and deliver material into tight, awkward and irregular areas because the cushioned portion of the applicator is able to compress into and around such areas, thereby achieving a desired delivery function.

The applicator may also be readily used as a cleaning device to clean such irregular and awkward areas. The cushioning effect of the cushioning member also assists the applicator in cleaning hard to reach, awkward, and uneven spaces. Thus, since the cushioned dental instruments (e.g., applicators) of the present invention readily fit into and adjacent crevices on teeth, the instruments can also be conveniently used as cleaning devices to clean teeth, gums, and adjacent surfaces.

According to another aspect of the invention, another object is to provide dental instruments with cushioned gripping portions that make it easier for the dentist to grip and control the instrument better.

It is yet another aspect of the invention, which may be employed with or without any other aspect of the invention, to provide a dental delivery instrument with which it is convenient to deliver a composition to the interior walls of dental preparation, such as a formed cavity or root canal. This may be accomplished, at least in part, by the provision of a dental delivery instrument in the form of a delivery tip or applicator having a plurality of fibers on a distal rim thereof and on the adjacent outer wall thereof.

A portion of the fibers extend a length "L" distally beyond the rim of the hollow body and a portion of the fibers are coupled along the tubular wall a distance "D" proximally with respect to the rim. In the present invention, the distance "D" is at least about two and one half times greater than the length "L" (i.e. D=at least about 2.5L). Thus, the distance covered by fibers coupled to the tubular wall is significantly greater than the length extended past the rim of the delivery instrument. A variety of ratios are possible, such as wherein D=2.5L, 3L, 4L, 5L, 6L, 7L, 8L, 9L, or 10L or any fraction thereof or greater. One advantage is that these ratios apply for a variety of different dental delivery instruments, such as those discussed herein.

Furthermore, by having fibers extending significantly along the length of the outer wall of the distal delivery end, it is possible to readily deliver and brush a dental composition both at the most remote point within a dental preparation and simultaneously along the interior wall surfaces of the preparation. The preparation may also be cleaned using the wall mounted fibers.

On the other hand, other delivery designs that do not feature such wall-mounted fibers extending such a distance "D" along the outer wall must be awkwardly maneuvered in order to enable the fibers to adequately touch the interior walls in a manner so as to coat the walls with the dental composition.

In the present invention, application of the dental composition to interior walls of a dental preparation can be achieved using the disclosed delivery devices by delivering a quantity of material into the dental preparation, then brushing the fibers against the bottom and/or interior walls using the disclosed delivery devices. Such brushing can also occur by delivering the composition from the orifice such that the composition contacts the rim fibers, then initially brushing a portion of a tooth (or other dental surface) with the rim fibers and continuing said brushing with the wall mounted fibers. In another embodiment, the rim fibers can be conveniently employed to remove bubbles from impression materials, while the wall fibers are employed to brush the impression material or another material onto a desired surface, such as an interior wall.

Furthermore, by having both: (i) fibers that extend outwardly from the distal delivery end of the delivery instrument substantially perpendicular to a face of the rim; and (ii) fibers that extend outwardly substantially perpendicular to the wall of the distal delivery end, a brushing motion can be achieved simultaneously at the interior wall of a cavity or canal and at the most remote point within the cavity or canal.

The fiber covered hollow delivery ends disclosed herein may be part of a delivery tip for delivering a variety of different materials such as restorative, bonding, or impression materials to the teeth and/or gums and/or may be part of a dental applicator or an endodontic irrigator for delivering various materials to a root canal.

These and other objects and features of the present invention will become more fully apparent from the following description and the appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not to be considered limiting of its scope, the invention will be described and explained with additional specificity and detail through the use of the accompanying drawings in which:

FIG. 1A is a perspective view of a delivery system of the present invention comprising: (i) a hollow delivery tip of the present invention having a cushioned, fiber covered distal delivery end and (ii) a syringe shown adjacent to a proximal receiving end of the delivery tip in a cutaway view.

FIG. 1B is a cross sectional side view of the delivery tip of FIG. 1A with the side fins removed.

FIG. 2 is a cross-sectional side view of an alternate delivery tip of the present invention having a layer of elastomeric material disposed about a notched portion of the distal delivery end and a plurality of fibers coupled to the elastomeric material.

FIG. 2A is a cross sectional, cutaway side view of an alternate delivery tip of the present invention comprising a layer of elastomeric material disposed about a rigid distal end of the delivery tip.

FIG. 2B is another cross sectional, cutaway side view of an alternate delivery tip of the present invention comprising a layer of elastomeric material disposed about a rigid distal delivery end.

FIG. 6A is a cross sectional side view of an alternate applicator of the present invention having a cushioned, fiber-covered distal tip member coupled to a distal end of a main body thereof.

FIG. 6B is a front view of the applicator of FIG. 6A with the fibers removed.

FIG. 7A is a cross sectional, cutaway side view of an alternate cushioned, fiber covered applicator of the present invention having a coating of elastomeric material disposed on a rigid distal end of a main body thereof.

FIG. 7B is a perspective, cutaway view of the applicator of FIG. 7A with the fibers removed.

FIGS. 9A and 9B demonstrate cross sectional views of extended and compressed embodiments, respectively, of a delivery system comprising a hollow applicator and a reservoir in fluid communication with an internal passageway of the applicator.

FIGS. 10A and 10B demonstrate cross sectional views of alternative extended and compressed embodiments, respectively, of a hollow applicator having a reservoir in fluid communication with an internal passageway of the applicator.

FIGS. 12A–12B demonstrate an alternate cushioned applicator tip member of the present invention having a spherical configuration with a groove therein.

FIGS. 13A–13B demonstrate an alternate cushioned applicator tip member of the present invention having a spherical configuration with a groove therein.

FIGS. 14A–14B demonstrate an alternate cushioned applicator tip member of the present invention having a spherical configuration with a groove therein.

FIGS. 15A–15B demonstrate an alternate cushioned applicator tip member of the present invention having a spherical configuration with a plurality of grooves therein.

DETAILED DESCRIPTION OF THE PREFERRED EMBODIMENTS

Figure 1C:
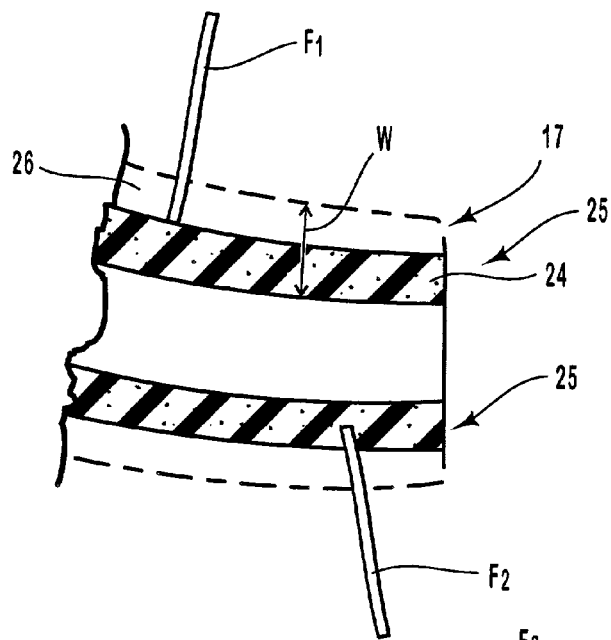
FIG. 1C is a cross sectional, cutaway side depiction of the elastomeric tip member shown in FIG. 1A with an optional adhesive coating shown in phantom lines.

This invention relates to cushioned dental instruments and/or flocked delivery devices. Examples of cushioned dental instruments are shown in the various Figures. The cushioned dental instruments of FIGS. 1A–2B comprise a dental delivery tip. The cushioned dental instruments of FIGS. 3A–31 comprise dental applicators. Each of these dental instruments comprises a main body having a proximal end and a distal end. Coupled to the distal end is an elastomeric member that acts as a cushioning member. The cushioning member can assist the practitioner in orienting the dental instrument into a difficult crevice or space, does not cause pain to teeth and gums, and acts as an efficient cleaning member, complying with rough, uneven and difficult crevices and spaces.

With specific reference now to FIGS. 1A–1B, delivery tip 10 comprises a hollow tubular body 12 having a hollow proximal receiving end 14 and a hollow distal delivery end 16. Tubular body 12 has a passageway extending from an inlet orifice at proximal end 14 to an outlet orifice at the tubular distal end 16. A distal rim 21 is located at distal delivery end 16. Tubular body 12 may have a variety of different configurations such as elongate, curved, straight, or irregular configurations or a variety of other configurations known to those skilled in the art.

As shown, a hollow, tubular elastomeric tip member 17 is coupled to rim 21 of tubular body 12. Member 17 acts as a cushioning member, and is substantially more deformable than the material of which body 14 is comprised. For example, in one embodiment, body 14 comprises a rigid polypropylene or polyethylene, while tubular elastomeric cushioning member 17 comprises a deformable elastomeric material, such as a thermoplastic elastomer, rubber, polyurethane, another elastomeric adhesive material, or another material that is thick enough to have a cushioning effect.

In the embodiment of FIGS. 1A and 1B, tip 10 further comprises a series of fibers coupled to elastomeric cushioning member 17, such as through electrostatic flocking.

Fibers 18 can be employed to remove particles from the mouth of the patient, to remove bubbles from an impression material or other material, to manipulate, massage, or clean appliances, teeth, gums, or other portions of the mouth, or for a variety of other purposes.

Delivery tip 10 is configured to be coupled to a delivery device, such as a syringe and to direct material delivered from syringe 19 to a desired location within the mouth of a patient. An external thread 20 is an example of a means for coupling tubular member 12 to a delivery device. Through the use of thread 20, tubular member 12 can be releasably coupled to a delivery device, such as syringe 19 (e.g., by being coupled to mating threads on syringe 19). However, a variety of different means for coupling tubular member 12 to a delivery device may also be employed, such as internal threads (e.g., thread 22 of FIG. 2), male or female Luer-lock type attachment members, a configuration that allows a press fit attachment, or any other suitable arrangement understood by one skilled in the art in light of the disclosure herein.

Syringe 19 may have a variety of different configurations. In one embodiment, syringe 19 comprises a reservoir means (e.g., a barrel) for holding a quantity of a dental composition for restorative or reconstructive dental procedures and a means for controlled dispensing (e.g., a plunger) of the dental composition from the reservoir means. The plunger or other means for controlled dispensing also dispenses the composition through the delivery tip in order to apply in a precise, controlled fashion the dental composition to a small area, such as a relatively small region of a tooth surface that is to be restored or reconstructed.

Examples of additional delivery tips, delivery devices, and methods of coupling such tips to such delivery devices are disclosed in U.S. Pat. No. 5,816,804 to Fischer, entitled Fiber-Ended Open Orifice Delivery Tip, which is incorporated herein in its entirety by reference.

Fibers 18 can have a variety of different lengths. In one embodiment, short and long fibers exist in a particular bundle of fibers such that the long fibers are supported by the short fibers. Optionally, fibers extend from distal rim 23.

Also as shown in FIGS. 2–2B, the elastomeric portion of the dental instrument of the present invention may be located on a variety of different portions of the main body of the dental instrument. In one embodiment, the elastomeric portion comprises a coating surrounding a rigid distal end portion, as shown in FIG. 2. FIG. 2 demonstrates an alternative delivery tip 30 of the present invention comprising a tubular body 31 having a hollow proximal receiving end 32 and a hollow distal delivery end 36. Distal delivery end 36 comprises a notched exterior portion. A surrounding elastomeric cushioning coating 38 is mounted on and extends about notched distal end 36. Elastomeric coating 38 comprises an elastomeric member, such as a thermoplastic elastomer or polyurethane as discussed above with respect to FIG. 1B. Fibers 40 extend from elastomeric coating 38. Fibers 40 can be affixed to coating 38 in a variety of different manners, such as through electrostatic flocking.

Since coating 38 surrounds notched distal end 36, coating 38 forms a substantially seamless distal end of delivery tip 30. This is advantageous because tip 30 can readily move smoothly within the mouth of a patient, rather than allowing a clump of adhesive material to become lodged or caught against a tooth or other structure as the distal end of tip 30 is moved in an out of the mouth. The shoulder 35 of the notched portion also forms a convenient surface for placing adhesive 38 on during the manufacturing process.

Figure 2C:
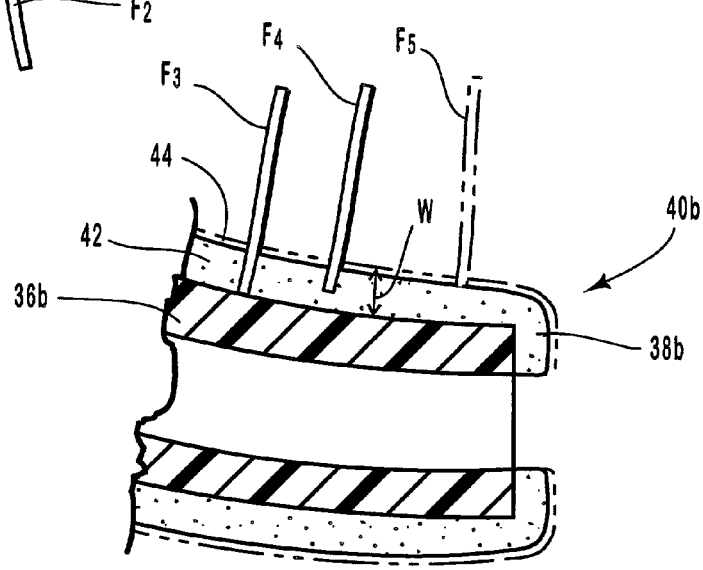
FIG. 2C is a cross sectional, cutaway side depiction of the coating and distal end shown in FIG. 2B with an optional adhesive coating shown in phantom lines.
Figure 2D:
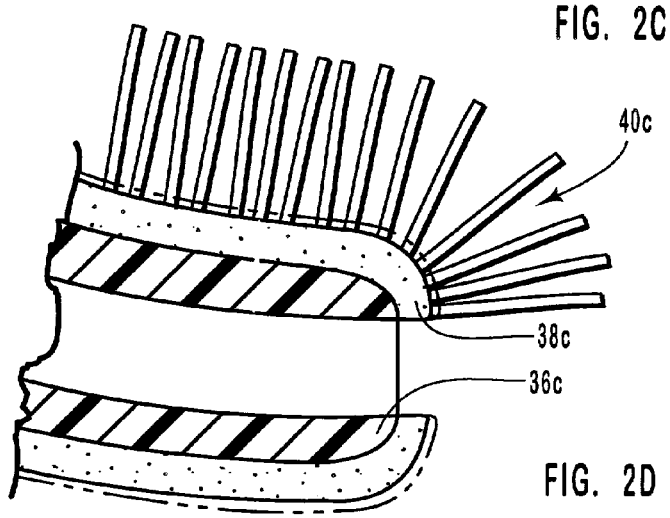
FIG. 2D is a cross sectional, cutaway side depiction of an optional coating and rounded distal end with an optional adhesive coating shown in phantom lines. Only one side is shown as flocked although both sides may be flocked.

The notched distal end can have a variety of different configurations, such as the configuration shown in FIG. 2 or the rounded configuration shown in FIG. 2*d*, for example. Thus, in one embodiment, the delivery tip featured in FIG. 2*d* has a shoulder 35 as shown in FIG. 2 against which the coating 38*c* abuts (and may have flocking fibers 40*c* on both sides thereof, coupled through electrostatic flocking, for example, rather than only one side thereof).

Thus, the elastomeric member of the present invention can be coupled to the distal delivery end of the main body in the form of a hollow tip member (e.g., FIG. 1A) or a coating (e.g., FIG. 2), for example. In addition, the fibers of the present invention may be mounted perpendicular to the elastomeric portion and/or may extend in a parallel relationship therewith, or in a variety of other configurations.

FIGS. 2A and 2B feature alternative distal delivery ends from that of FIG. 2, with the remainder of body 31 being the same as in FIG. 2 in one embodiment. In the embodiment of FIG. 2A, rigid distal end 36*a* of body 31 does not notch inwardly, but rather, has an exterior surface that is relatively flush with the remainder of tubular body 31. Elastomeric coating 38*a* extends about the rigid delivery end 36*a* of body 31 and has fibers 40*a* mounted thereon, such as through electrostatic flocking.

In yet another embodiment, as shown in FIG. 2B, elastomeric coating 38*b* is mounted about the distal end 36*b* of body 31 and/or on the distal rim 39*b* of distal end 36*b* and has fibers 40*b* mounted thereon, such as through electrostatic flocking.

In yet another embodiment of the present invention (not shown), an elastomeric material is disposed on the internal diameter of the distal end of the delivery tip and has fibers coupled thereto, such as through electrostatic flocking. Such a tip can be comprised of metal or plastic, for example, while the elastomeric material comprises a thermoplastic elastomer, or polyurethane, also by way of example.

Another cushioned delivery tip of the present invention comprises an elastomeric member coupled to a tubular member of a delivery tip disclosed in U.S. Pat. No. 5,816,804 to Fischer, entitled Fiber-Ended Open Orifice Delivery Tip, which is incorporated herein by reference, and has fibers mounted on the elastomeric member, such as through electrostatic flocking. The hollow tip member (e.g., member 17) and the coating (e.g., coatings 38, 38*a*, 38*b*, 38*c*), maybe flocked in a variety of different manners. For example, as shown in FIG. 1C, in one embodiment, a wall 25 of hollow tip member 17 comprises a base 24 and an adhesive layer 26, shown in phantom lines. Flocking fibers $F^1$ may be placed on adhesive coating 26 and adhered thereto, such as through electrostatic flocking. Thus, with reference to FIG. 1C, in one embodiment, tip member 17 comprises a base 24 of elastomeric material having an adhesive coating 26 thereon for maintaining fibers thereon. However, fibers may be coupled to tip member 17 in a variety of different manners. Optionally, fibers $F^2$ are embedded into base 24 of elastomeric tip member 17 (with or without adhesive layer 26) to maintain the fibers therein. Base 24 may comprise an elastomeric material, an elastomeric adhesive material (e.g., polyurethane), a series of elastomeric adhesive coating materials placed sequentially onto one another, a molded elastomeric member or a variety of different possible members that maintain the fibers therein. As yet another option, adhesive 26 is also an elastomeric material, possibly the same material used for base 24 (e.g., polyurethane). Thus, it is possible for base 24 and adhesive coating 26 to be the same material, such as polyurethane, for example, or different materials. Optionally, fibers are coupled to base 24 with or without an adhesive layer 26 through insert or injection molding.

With continued reference to FIG. 1C, in one embodiment, the width W of wall 25 of elastomeric tip member 17 (with or without adhesive layer ) is in the range of about 0.2 mm to about 4 mm, more preferably about 0.3 mm to about 2.5 mm, most preferably about 0.4 mm to about 1.8 mm. Also with reference to FIG. 1C, in another embodiment, the width W is greater than about 1 mm, such as in the range of: (i) greater than about 1 mm; to (ii) about 4 mm. A variety of different widths may be employed, however, depending upon a desired application.

The tip coatings (e.g., coatings 38, 38a, 38b, 38c) of the present invention may also be flocked in a variety of different manners. For example, in one embodiment, elastomeric coating 38b comprises a base 42 and an adhesive coating 44, shown in phantom lines in FIG. 2c. In this embodiment, base 42 can be formed by coupling base 42 to a rigid body 36b, such as through molding or adhesion, after which adhesive coating 44 is placed on base 42. Next, flocking fibers $F^5$ are placed on adhesive coating 44 and adhered thereto, such as through electrostatic flocking.

Thus, with reference to FIG. 2C, in one embodiment, coating 38b comprises a base 42 of elastomeric material having an adhesive coating 44 thereon for maintaining fibers thereon.

However, fibers may be coupled to end 36b in a variety of different manners. Optionally, fibers $F^3$, $F^4$ are embedded into base 36b (with or without adhesive layer 44) to maintain the fibers therein. Base 42 may comprise an elastomeric material, an elastomeric adhesive material, a series of elastomeric adhesive coating materials placed sequentially onto one another, a molded elastomeric member or a variety of different possible members that maintain the fibers therein. As yet another option, adhesive 44 is also an elastomeric material, possibly the same material used for base 42. Thus, it is possible for base 42 and adhesive coating 44 to be the same material (e.g., polyurethane) or different materials, for example. Optionally, fibers are coupled to base 42 with or without an adhesive layer through insert or injection molding.

In one embodiment, the width W of the elastomeric coating 38b (with or without adhesive layer) is in the range of about 0.1 mm to about 2 mm, more preferably about 0.2 mm to about 1 mm, most preferably about 0.25 mm to about 0.8 mm. In yet another embodiment, the width W is in the range of greater than about 0.5 mm, such as in the range of: (i) greater than about 0.5 mm; to (ii) about 2 mm. Coatings 38a, 38c may have the same dimensions as those described with respect to coating 38b, for example, although a wide variety of ranges are available.

Figure 3A:
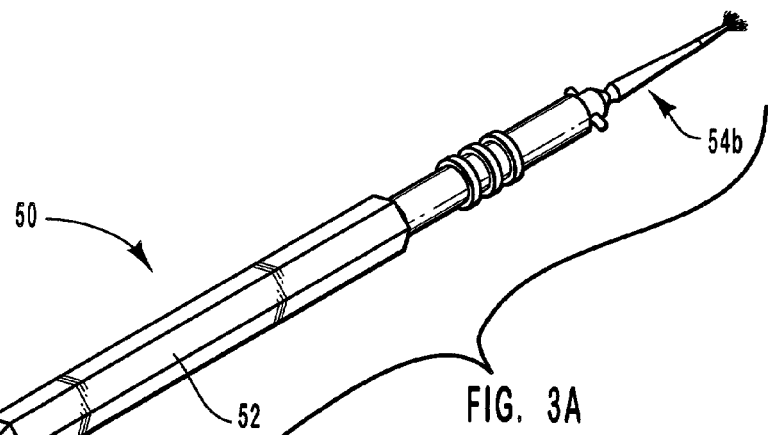
FIG. 3A is a perspective view of an applicator of the present invention having first and second cushioned, fiber covered tips on opposing ends thereof.
Figure 3D:
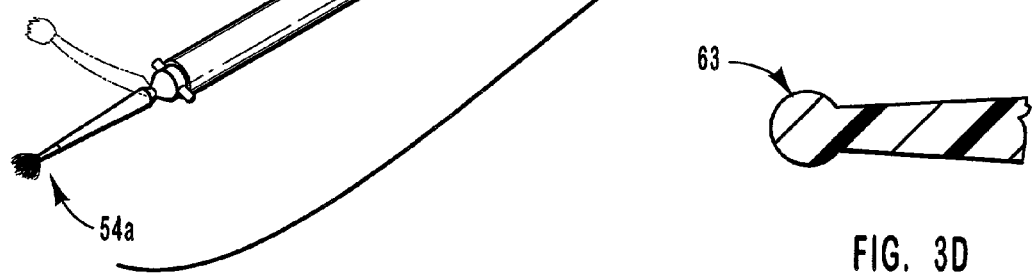
FIG. 3D is a cross sectional, cutaway view of another applicator tip of the present invention.
Figure 3B:
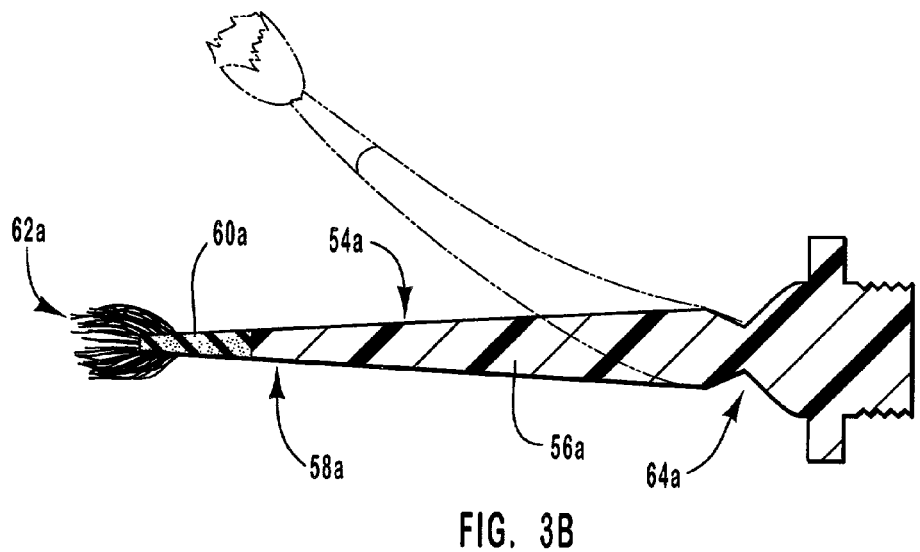
FIG. 3B is a cross sectional side view of a cushioned tip of the applicator of FIG. 3A comprising an elastomeric member that forms a distal cushioned tip member thereof.
Figure 3C:
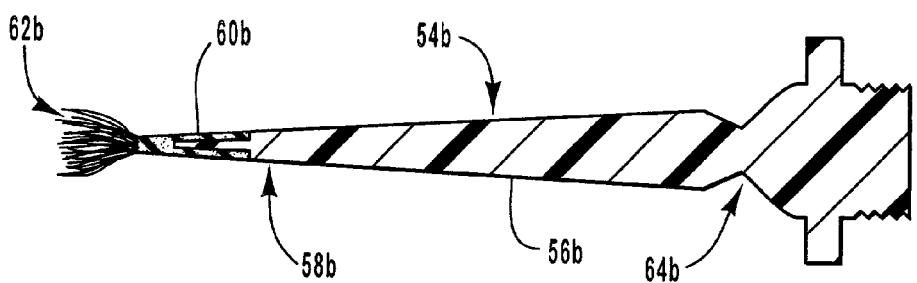
FIG. 3C is a cross sectional side view of another tip of the applicator of FIG. 3A.

Another embodiment of the present invention is shown in FIG. 3A, which features an applicator 50 of the present invention. Applicator 50 has: (i) an elongate main body 52; and (ii) first and second applicator tips 54a and 54b mounted on body 52. Tips 54a and 54b are shown in FIGS. 3B and 3C, respectively. Each tip 54a, 54b comprises an elongate main body portion 56a and 56b having a respective proximal end 64a, 64b and a respective distal delivery end 58a and 58b. Each delivery end 58a, 58b has an elastomeric member 60a and 60b, respectively, coupled thereto. A plurality of fibers 62a and 62b, respectively, are coupled to the elastomeric member, such as through electrostatic flocking or through a variety of other methods.

It will be appreciated that an applicator of the present invention may comprise first and second tips which are configured as shown in FIGS. 3B or 3C, or a variety of other configurations. For example, a tip may be configured as shown in FIG. 3D, which features a paddle shaped tip 63 and may have an elastomeric material and flocking fibers thereon. It is possible to couple the elastomeric member of the present invention to the rigid material in a variety of different manners, such as by mounting the elastomeric member 60a on the end of the distal delivery end 58a, as shown in FIGS. 3B, or by forming a cap of elastomeric material 60b, as shown in FIG. 3C. This may be accomplished through a variety of different methods, such as two-color molding, three color molding, adhesion, ultrasonic bonding or a variety of other methods known in the art.

Fibers 62A and/or 62B can have a variety of different lengths. In one embodiment, short and long fibers exist in a particular bundle of fibers such that the long fibers are supported by the short fibers.

As shown in the phantom lines of FIGS. 3A and 3B, in one embodiment, tip 54a may be bent, such that the tip may be manipulated into a desired location. This may be accomplished, for example, by employing a grooved portion at proximal end 64a that is substantially thinner than the remainder of the tip body 56a, such that the tip can be bent into a desired location. The thinner grooved portion allows the distal delivery end of the tip to be selectively bent with respect to the more proximal gripping end. The applicator body may optionally be hollow in order to allow the distal end to bend more readily and to conserve material.

The elastomeric members of the applicators disclosed herein act as cushioning members, and are substantially more deformable than the material of which the body of the applicator is comprised. For example, in one embodiment, the applicator body (and tip bodies 56a, 56b, for example) comprises a rigid polypropylene or polyethylene, while the elastomeric cushioning member comprises a deformable elastomeric material, such as a thermoplastic elastomer, rubber, polyurethane, another elastomeric adhesive material, or another material that is thick enough to have a cushioning effect.

It will be appreciated in light of the disclosure herein that each tip 54a, 54b can itself be used independently as an applicator comprising a main body 56a, 56b having a proximal gripping end 64a, 64b and a distal delivery end 58a, 58b. Thus, each such tip 54a, 54b can also be considered to be an applicator as defined and claimed herein.

Figure 4A:
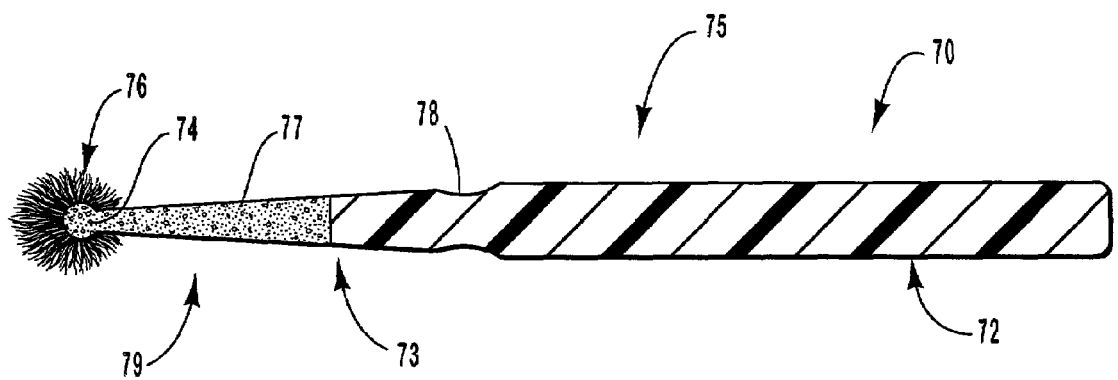
FIG. 4A is a cross sectional side view of an alternate applicator of the present invention having a cushioned, fiber-covered distal tip member coupled to a distal end of a main body thereof.
Figure 4B:
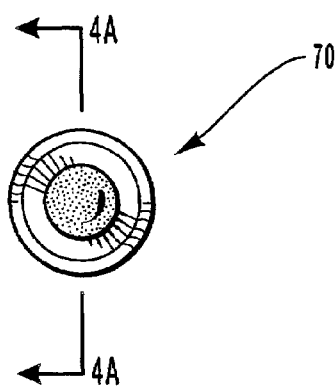
FIG. 4B is a front view of the applicator of FIG. 4A with the fibers removed.

Yet another embodiment of an applicator 70 of the present invention is shown in FIGS. 4A and 4B. Applicator 70 has an elongate, rigid main body 75 having a proximal gripping end 72 and a distal end 73. An elastomeric member 79 is coupled to the distal end 73. The elastomeric member 79 includes a spherically shaped elastomeric member 74 coupled to an elongate elastomeric member 77 to form an elastomeric tip member 79. The length of member 77 may vary depending upon a desired application. In another embodiment, rather than employing elastomeric member 77, rigid body 75 extends to spherically shaped elastomeric member 74 and is coupled thereto. Elongate body 75 has an annular groove 78 therein that allows a distal portion of the body to be bent with respect to a proximal portion thereof. Body 75 can be hollow or solid.

Elastomeric tip member 79 enables a practitioner to readily deliver a desired material to difficult to reach places, crevices, cracks and spaces between teeth, in light of the deformable nature thereof. Member 79 conforms to a delivery location even if the location is rough and cracked. Such delivery can be performed without injuring the patient.

In the embodiment of FIG. 4A, the spherical portion 74 of tip member 79 is covered with a fibrous covering 76 comprising a series of fibers 76. However, fibers 76 are optional, as shown in FIG. 4B, which demonstrates a front end view of applicator 70 without fibers. Such a nonfibrous applicator 70 can be used to deliver materials to a desired location without injury and while conforming to a desired delivery location.

Nevertheless, fibers 76 are highly useful in that they can be used for massaging, manipulating, removing bubbles, cleaning, or for a variety of other purposes. Fibers 76 can be attached to tip member 79 through flocking, such as electrostatic flocking, for example, and may comprise both long and short fibers such that the short fibers support the longer fibers.

Tip member 79 can be flocked in a variety of different manners. For example, in one embodiment, spherical portion 74 comprises a base 80 (FIG. 4c) and an adhesive layer 82, shown in phantom lines. In this embodiment, base 80 can be formed by coupling base 80 to a rigid body or an elastomeric member 77 such as through molding or adhesion, after which adhesive coating 82 (FIG. 4C) is placed on base 80. Optionally, base 80 is integral with member 77, which is coupled to rigid body 75, such as through molding or adhesion. Following the placement of coating 82 on base 80, flocking fibers $F^1$ are placed on adhesive coating 82 and adhered thereto, such as through electrostatic flocking. Thus, with reference to FIG. 4C, in one embodiment, spherical portion 74 comprises a base 80 of elastomeric material having an adhesive coating 82 thereon for maintaining fibers thereon.

However, fibers may be coupled to tip member 79 in a variety of different manners. Optionally, fibers $F^2$ are embedded into base 80 of elastomeric tip member 79 (with or without adhesive layer 82) to maintain the fibers therein. Base 80 may comprise an elastomeric material, an elastomeric adhesive material (e.g., polyurethane), a series of elastomeric adhesive coating materials placed sequentially onto one another, a molded elastomeric member or a variety of different possible members that maintain the fibers therein. As yet another option, adhesive 82 is also an elastomeric material, possibly the same material used for base 80. Thus, it is possible for base 80 and adhesive coating 82 to be the same material, such as polyurethane, or different materials, for example. Optionally, fibers are coupled to base 80 with or without an adhesive layer through insert or injection molding.

Figure 4C:
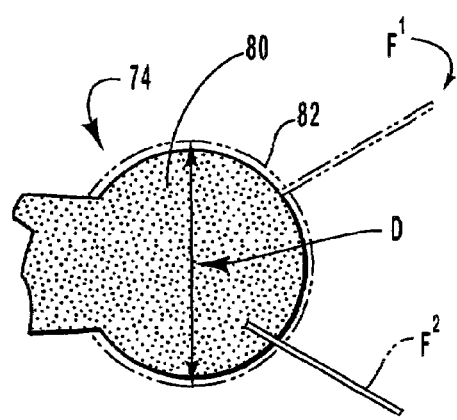
FIG. 4C is a cutaway depiction of the distal tip member of FIG. 4A demonstrating various options for coupling fibers to the elastomeric distal tip member.

With continued reference to FIG. 4C, in one embodiment, the diameter D of the spherical portion 74 of the elastomeric tip member 79 (with or without adhesive layer 82) is in the range of about 0.2 mm to about 4 mm, more preferably about 0.3 mm to about 2.5 mm, most preferably about 0.4 mm to about 1.8 mm. Also with reference to FIG. 4C, in another embodiment, the diameter D is greater than about 1 mm, such as in the range of: (i) greater than about 1 mm; to (ii) about 4 mm.

Figure 5A:
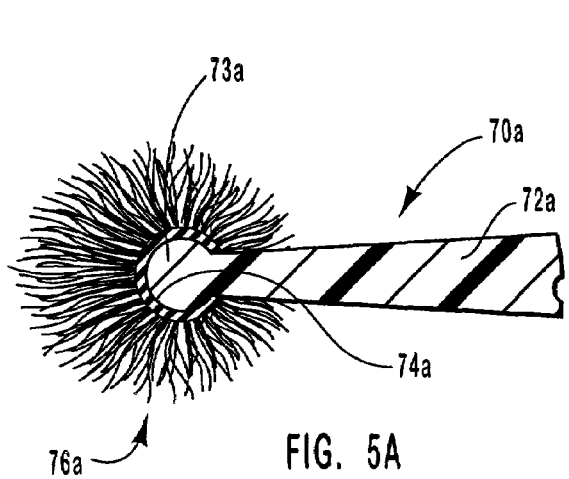
FIG. 5A is a cross sectional, cutaway side view of an alternate cushioned, fiber covered applicator from that of FIG. 4A having a coating of elastomeric material disposed about a rigid distal end of a main body thereof.

FIG. 5A demonstrates another embodiment of an applicator 70a comprising an elastomeric member in the form of a coating 74a deposited on a spherically shaped rigid distal delivery end 73a of a rigid body portion 72a, which is shown in a cutaway view. The elastomeric coating 74a cushions the contact of the instrument 70a against the teeth and gums of a patient. Fibers 76a can include short and long fibers such that the long fibers are supported by the short fibers, for example.

Elastomeric coating 74a can be flocked in a variety of different manners. For example, in one embodiment, elastomeric coating 74a comprises a base 80a (FIG. 5B) and an adhesive coating 82a, shown in phantom lines. In this embodiment, base 80a can be formed by coupling base 80a to a rigid body 73, such as through molding or adhesion, after which adhesive coating 82a (FIG. 5B) is placed on base 80a. Next, flocking fibers $F^5$ are placed on adhesive coating 82a, and adhered thereto, such as through electrostatic flocking.

Figure 5B:
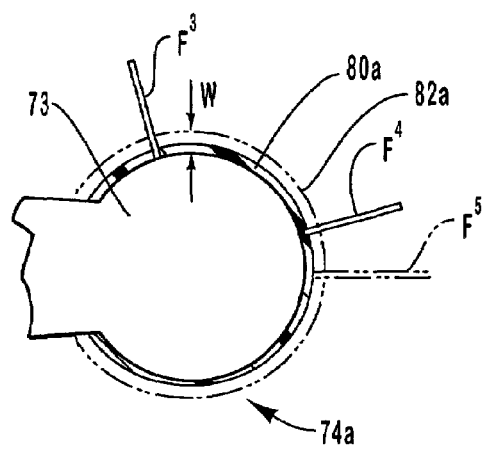
FIG. 5B is a cutaway depiction of the distal tip member of FIG. 5A demonstrating various options for coupling fibers to the elastomeric coating.

Thus, with reference to FIGS. 5A–5B, in one embodiment, coating 74a comprises a base 80a of elastomeric material having an adhesive coating 82a thereon for maintaining fibers thereon.

However, fibers 76a may be coupled to end 73a in a variety of different manners. Optionally, fibers $F^3$, $F^4$ are embedded into base 80a (with or without adhesive layer 82a) to maintain the fibers therein. Base 80 may comprise an elastomeric material, an elastomeric adhesive material, a series of elastomeric adhesive coating materials placed sequentially onto one another, a molded elastomeric member or a variety of different possible members that maintain the fibers therein. As yet another option, adhesive 82a is also an elastomeric material, possibly the same material used for base 80a. Thus, it is possible for base 80a and adhesive coating 82a to be the same material, such as polyurethane, or different materials, for example. Optionally, fibers are coupled to base 80 with or without an adhesive layer through insert or injection molding.

In one embodiment, the width W of the elastomeric coating 74a (with or without adhesive layer 82a) is in the range of about 0.1 mm to about 2 mm, more preferably about 0.2 mm to about 1 mm, most preferably about 0.25 mm to about 0.8 mm. In yet another embodiment, the width W is in the range of greater than about 0.5 mm, such as in the range of: (i) greater than about 0.5 mm; to (ii) about 2 mm.

In yet another embodiment of the present invention, the dental tool of the present invention comprises an elongate rigid body coupled to a flocked elastomeric member (such as a spherical elastomer as in FIG. 4c, 6a, or 31 or an elastomer having other shapes described herein), the elastomeric member having a diameter D in the range of about 4 mm to about 40 mm. This tool may act as a brush, for example. Optionally, the brush is configured as shown in FIG. 5A and the elastomeric coating thereof has a width in the range of about 2 mm to about 20 mm.

Thus, in one embodiment of an instrument of the present invention, comprising a rigid body and a flocked elastomeric member, the elastomeric member has a diameter D in the range of about 0.2 mm to about 40 mm depending upon the embodiment. Optionally, the tool is configured as shown in FIG. 5A and the elastomeric coating thereof has a width in the range of about 0.1 mm to about 20 mm.

With reference now to FIGS. 6A–6B, another applicator 90 comprises an elongate body 92 and an elastomeric member in the form of a spherically shaped or paddle-shaped tip member 94 coupled to a distal end 95 of elongate body 92. Elastomeric member 94 optionally has fibers 96 coupled thereto, such as through electrostatic flocking. Elastomeric member 94 is shown without such flocking and having a paddle shape in a front view in FIG. 6B. Flocking 96 may be applied through a variety of different methods, such as electrostatic flocking or other methods known in the art. Elastomeric member 94, whether in a paddle or spherical shape can have the same or similar dimensions as discussed above with respect to member 74, for example.

A paddle shaped for tip member 94, as shown in FIG. 6B is highly useful in that it can be used as a scoop, a flattener or for a variety of different purposes. The entire paddle 94 may comprise an elastomeric portion.

In another embodiment of an applicator, however, as shown in FIGS. 7A–7B, an elastomeric member in the form of an elastomeric coating 94a covers the paddle-shaped distal delivery end 95a of a rigid elongate body member 92a. Fibers 96a can include short and long fibers such that the long fibers are supported by the short fibers. Coating 94a can have the same or similar dimensions as discussed above with respect to coating 74a, for example.

It will thus be appreciated from the present invention that the elastomeric member of the dental instrument of the present invention may have a variety of different shapes and configurations, such as: (i) a hollow elastomeric tip member 17, as shown in FIGS. 1A–1B, (ii) a coating as shown in FIGS. 2, 5A, and 7A (iii) a solid tip member as shown in FIGS. 3A–3C, 4A, and 6A and a variety of other configurations. Each of these elastomeric members may be coupled to a corresponding rigid member through a variety of methods, such as two-color molding, three color molding, adhesion, ultrasonic bonding, insert or injection molding, or a variety of other methods known in the art.

The following discussion with regard to materials to be used and coupling methods can apply both to applicators and delivery tips. As mentioned above, in one embodiment, the body of a delivery tip or applicator comprises a rigid polypropylene or polyethylene, while the elastomeric cushioning member coupled thereto comprises a deformable elastomeric material, such as a thermoplastic elastomer, rubber, polyurethane, another elastomeric adhesive material, or another material that is thick enough to have a cushioning effect.

Coupling of the elastomeric member, and optionally a nonslip cushioned grip as discussed with reference to FIGS. 19–31, to the rigid body of the delivery tip or applicator may be accomplished through a variety of different methods, such as two-color or three, four, five, or six color molding, insert or injection molding, other molding processes, adhesion, ultrasonic bonding (e.g., thermoplastic elastomer to polypropylene), or a variety of other methods known in the art. Additional additives can be employed in the molding process to improve adhesion. Coupling can be enhanced through a mechanical bond such as by shaping the rigid plastic with a notch, such as an undercut or groove to receive a portion of the elastomeric member to assist in mechanically bonding a portion of the elastomeric member to the rigid body.

Also as previously mentioned, in one embodiment, the elastomeric member comprises an elastomeric adhesive, such as polyurethane. In this embodiment, the adhesive member placed on a rigid delivery tip body or rigid applicator body can itself be electrostatically flocked to form a cushioned, electrostatically flocked delivery tip. The elastomeric adhesive is employed in thicknesses sufficient to provide an elastomeric, cushioned effect. Optionally, the elastomeric member may comprise a combination of an adhesive and another elastomeric material coupled to the adhesive.

As yet another option, in one embodiment, the elastomeric member comprises a series of layers that are built up upon each other to form the elastomeric layer. For example, in one embodiment, a first layer is placed on the applicator body or delivery tip body, after which the layer is cured. Next, a second layer is placed on the first layer and cured. Additional layers can be added as desired. Optionally, a single elastomeric layer is employed.

The durometer of the thermoplastic elastomer or other elastomeric member coupled to the applicator or delivery tip may vary with the viscosity of the material to be delivered. For example, when a higher viscosity impression material is to be delivered, it may be desirable to employ a higher durometer thermoplastic elastomer to more effectively manipulate the more viscous impression material. On the other hand, when delivering a lower viscosity material, such as an etching material, it may be desirable to employ a lower durometer elastomeric member in order to provide more cushioning.

It is possible to practice the present invention without the use of flocking fibers, i.e., through the use of a delivery tip or applicator having the described elastomeric portions without the use of flocking fibers thereon. Nevertheless, the fibers can be employed on the delivery tips and/or applicators to remove particles from the mouth of a patient, to remove bubbles from an impression material or other material, to manipulate or massage appliances, teeth, gums or portions of the mouth, or for a variety of other purposes.

The stimulation provided by the fibers also results in better adaptation of the applied material around tooth surfaces. The fibers may also be used in a brushing or scrubbing action, which is advantageous for working other dental compositions into the tissues. The fibers can also be used for cleaning. If the elastomeric member, with the fibers mounted thereon, contacts the tooth or gums of a patient during delivery of material or during removal of air bubbles or other procedure, such contact will not harm or injure the patient. Fibers can be disposed in spaced apart clumps around the elastomeric portion or surround the entire elastomeric portion. In each of the embodiments disclosed herein employing fibers, the fibers can include short and long fibers such that the long fibers are supported by the short fibers. The fibers may be coupled to the elastomeric member in a variety of different manners, such as through flocking, e.g., electrostatic flocking, gravity flocking, and a variety of other flocking methods. Such flocking may occur through a variety of different procedures, such as disclosed in U.S. patent application Ser. No. 09/496,275 to Rachal, et al, filed on Feb. 1, 2000 entitled "Electrostatically Flocked Fishing Lures and Related Systems and Methods," which is incorporated herein by reference.

According to one flocking method, an adhesive material is applied where fiber attachment is desired. An appropriate quantity of fibers is then contacted with the adhesive material. The adhesive is allowed to harden, thereby securing the fibers to the desired portion. The adhesive can be an adhesive coating and/or a portion of an adhesive base 1 material.

An additional method of fiber attachment is to injection or insertion mold the fibers onto the desired elastomeric member. Thus, the fibers and elastomeric member can each be injection or insertion molded, either by (i) initially injection or insertion molding the elastomeric member onto the rigid applicator or delivery tip body, followed by insertion or injection molding of the fibers onto the elastomeric member; or (ii) simultaneously injection or insertion molding the elastomeric member onto the rigid body and the fibers onto the elastomeric member, for example. Such molding can occur with a plastic material (possibly the same or different materials). Thus, in one embodiment, the fibers are in a diameter and length which allows injection or insertion molding.

Both natural and synthetic fibers may be used. Suitable natural fibers include cotton fibers, while suitable synthetic fibers include nylon and polyester fibers. In addition, as mentioned, various injection moldable plastics can be employed to form the fibers of the present invention using standard injection molding techniques. Other fiber types, sizes, and shapes that are useful in the present invention are disclosed in U.S. patent application Ser. No. 09/496,275 to Rachal, et al, filed on Feb. 1, 2000 entitled "Electrostatically Flocked Fishing Lures and Related Systems and Methods."

In one embodiment, the rigid main body portion of a particular delivery tip or applicator comprises a rigid material such as polypropylene or polyethylene, the elastomeric member comprises a deformable material and the fibers mounted on the elastomeric member comprise: (i) a deformable material; or (ii) a rigid material. The elastomeric member is more deformable than the rigid main body and the fibers can be more rigid, less rigid, or have the same rigidity as the material employed for the main body of the delivery tip or applicator. This can be achieved, for example, through three color molding or through insert or injection molding. Four or five color molding can be used if a non-slip grip is employed, for example.

For example, in one embodiment, the rigid main body portion of a particular delivery tip or applicator comprises a rigid material such as polypropylene or polyethylene, the elastomeric cushioning member comprises an elastomeric thermoplastic elastomer that is softer than the applicator body or delivery tip body and the fibers comprise a thermoplastic elastomer having a higher durometer than the delivery tip body or applicator body. Optionally, the fibers comprise a polypropylene, polyethylene or another material having a hardness comparable to polypropylene or polyethylene.

In another embodiment of the present invention, the fibers comprise a material that is less rigid than the elastomeric cushioning material of a particular delivery tip or applicator. In yet another embodiment, the fibers comprise a material that has the same rigidity as the elastomeric cushioning material. For example, in this embodiment, the fibers and cushioning material are formed from the same material.

Also by way of example, in one embodiment, the rigid body portion of a particular delivery tip or applicator comprises polypropylene or polyethylene, the elastomeric member comprises a softer thermoplastic elastomer, rubber, polyurethane, or other deformable material and the fibers mounted on the elastomeric member comprise an injection or insertion molded thermoplastic elastomer. Such an injection molded thermoplastic elastomer 1 may have a higher durometer than the elastomeric member. Optionally, the fibers comprise polypropylene, polyethylene or another material having a hardness comparable to polypropylene or polyethylene. This may be achieved through two or three color molding, insert or injection molding, for example.

The dental tool of the invention can be made with thinner fibers or with thicker fibers. For example, the tool made with thinner fibers may be useful in delivering compositions such as sealing agents that need to be "spread" or "painted" onto tooth surfaces. The delivery tip made with thicker fibers can be useful in delivering and agitating higher viscosity materials, such as impression materials and other appropriate materials, for example.

In one embodiment, the length of the fibers of the delivery tips disclosed herein is in the range from about 0.3 mm to about 5 mm, preferably about 0.3 mm to about 3 mm, and more preferably from about 0.5 mm to about 2 mm. In this embodiment, the diameter of the fibers of the delivery tips may be in the range from about 1 Denier to about 15 Denier, and more preferably in the range from about 1.5 Denier to about 10 Denier, for example. This embodiment may be useful for delivering sealing agents, for example.

In yet another embodiment, such as when higher viscosity materials (e.g., impression materials) are employed, the length of the fibers may be in the range from about 0.3 mm to about 5 mm, preferably about 1 mm to about 3 mm, and more preferably from about 1.5 mm to about 2 mm. The diameter of such fibers may be in the range from about 3 Denier to about 75 Denier, about 3 Denier to about 45 Denier, and more preferably in the range from about 6 Denier to about 20 Denier, for example. This embodiment may be useful for removing bubbles in impression material, for example.

Also by way of example, the fiber length for the fibers of the applicators disclosed herein may be in the range from about 0.3 mm to about 3 mm, preferably from about 0.5 mm to about 2 mm, more preferably from about 0.7 mm to about 1.5 mm, such as about 1 mm, for example. In one embodiment, the fiber diameter of the applicators is in the range from about 1 Denier to about 45 Denier, preferably about 1.5 Denier to 20 Denier, and more preferably in the range from about 1.5 Denier to about 10 Denier.

However, these ranges are highly dependent upon viscosities of materials employed, surface tensions, cohesiveness, and other physical properties. Brushes of the present invention may have a variety of different lengths of fibers, such as about 3 mm to about 20 mm in one embodiment, although other ranges are possible, including longer and shorter fibers. Such brushes may require larger diameter fibers than other instruments of the present invention, although the exact sizes depend upon a desired use.

In a preferred embodiment, the adhesive used to attach the fibers to the body or elastomeric portion of the tool is water insoluble. It is also important that the components of the dental tool will not react with a dental composition used therewith. In addition, the dental composition should not adhere to the construction materials used. Since many dental compositions are light sensitive, the construction materials used may be light-resistive. For example, various colored plastics that tend to filter out light can be employed in making the dental tool.

The elastomeric members disclosed herein and coupled to the distal ends of the main bodies of the applicators and delivery tips disclosed are examples of means for cushioning the distal ends of the main bodies. The dental tools described can be formed in a variety of different shapes and sizes and the sizes illustrated have been provided by illustration only.

Figure 8A:
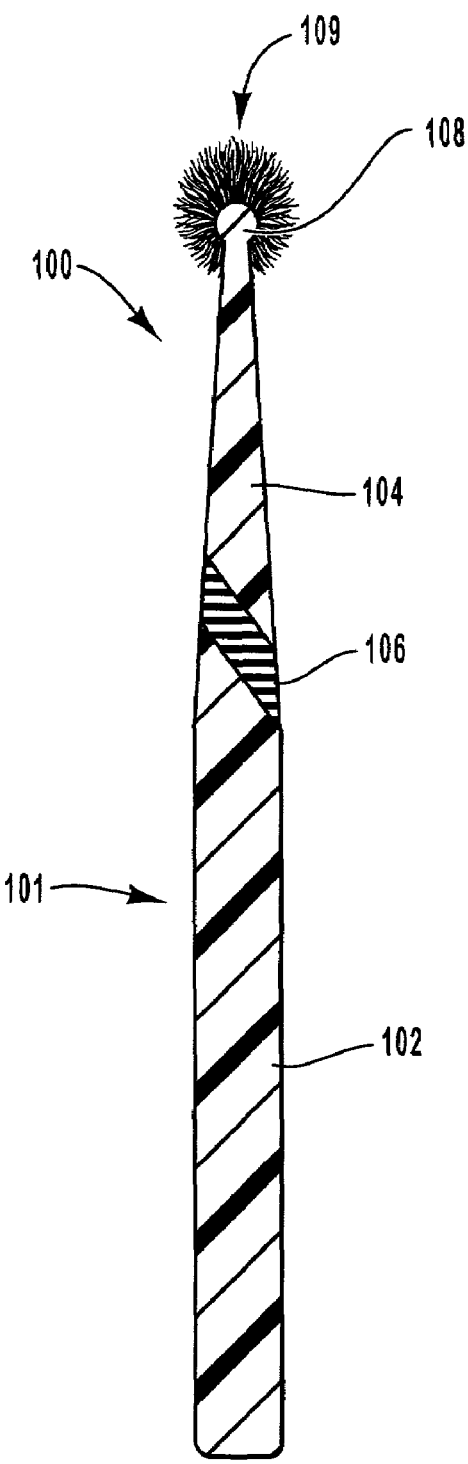
FIGS. 8A and 8B demonstrate cross sectional views of alternative applicators of the present invention having an elastomeric member that flexibly connects a proximal body portion to a distal body portion. In the embodiment of FIG. 8B, the distal body portion has a cushioned distal end coupled thereto.
Figure 8B:
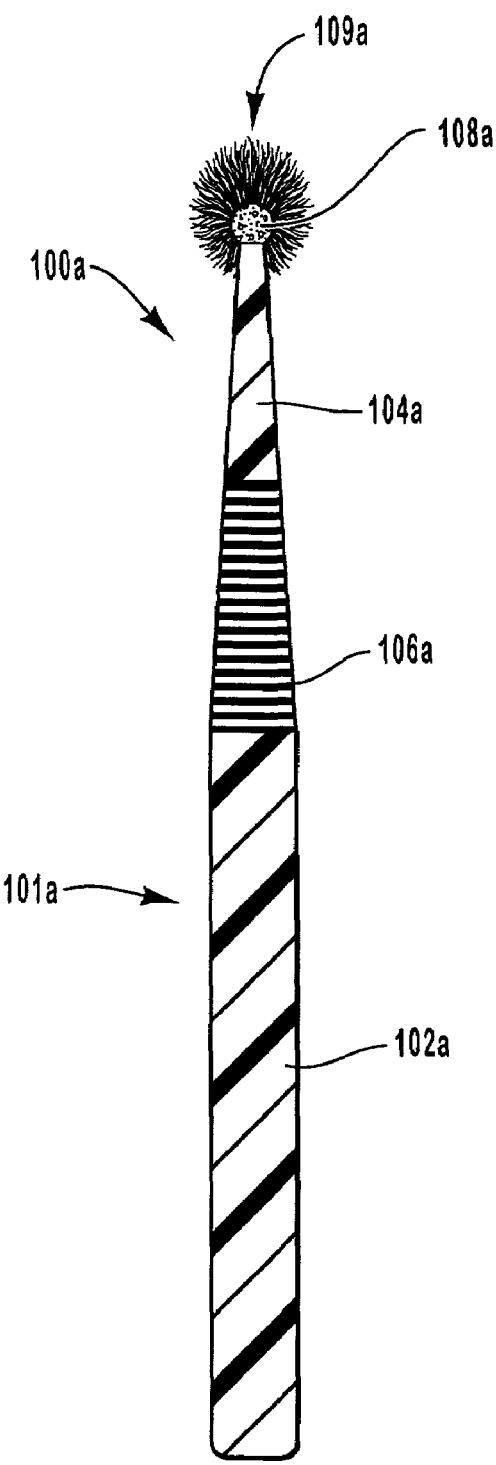

Reference will now be made to FIGS. 8A and 8B. FIGS. 8A and 8B demonstrate alternative applicators 100, 100a of the present invention. Each applicator 100, 100a has a main body 101, 101a. The main body of each applicator comprises a rigid proximal gripping end 102, 102a; a rigid distal delivery end 104, 104a and an elastomeric member 106, 106a that couples proximal gripping end 102, 102a to distal delivery end 104, 104a. As shown, the elastomeric member 106, 106a may have a variety of different shapes. The applicator may have a rigid distal delivery tip member 108 or may have an elastomeric tip member 108a coupled to the distal delivery end 104, 104a. The rigid distal delivery tip member 108 or elastomeric tip member 108a can have fibers 109, 109a flocked thereon, such as through electrostatic flocking, or may have the fibers coupled thereto through another method. Thus, the distal delivery end may have fibers directly coupled thereto, or indirectly coupled thereto (e.g., by having the fibers coupled to an elastomeric member).

It may be advantageous for an applicator to have an elastomeric material dividing a first rigid member from a second rigid member, as shown in FIGS. 8A and 8B. For example, certain materials require the use of a rigid distal delivery end for delivery thereof. In addition, certain chemicals to be delivered are most compatible with certain rigid materials, such as polypropylene. Nevertheless, it may be desirable to enable the tool to still flex in certain areas. The elastomeric transition section can enable a practitioner to achieve each of these goals and reach a desired location within a patient's mouth, for example, which requires flexibility.

Optionally, it may be desirable to employ an applicator having a proximal rigid body, an elastomeric transition section, and a distal section coupled to the elastomeric transition section that is also elastomeric, but is more rigid than the transition section. Such an embodiment is also possible according to the present invention. With reference now to FIGS. 9A and 9B, another embodiment of a dental applicator 200 comprises a hollow rigid main body 202 and an elastomeric member 204 coupled to the hollow main body 202. Elastomeric member 204 has fibers 206 thereon. Fibers 206 are deposited, for example, through electrostatic flocking. Elastomeric member 204 has a hollow channel 208 extending therethrough. Channel 208 is in fluid communication with a channel 216 in hollow main body 202. Channels 208, 216 enable fluid to flow through body 202 and elastomeric member 204. Channel 208 is an example of means for enabling fluid to flow through elastomeric member 204. Another example of means for enabling fluid to flow through elastomeric member comprises elastomeric member 204 being configured from a permeable material, through which a fluid may flow.

One advantage of such a hollow main body 202 of applicator 200 is that hollow main body 202 may be movably coupled in fluid communication with a reservoir, such as reservoir 210. Reservoir 210, main body 202 and elastomeric member 204 collectively form a delivery system. As one option, the delivery system conveniently acts as a "unit dose applicator 200" that can be conveniently used to deliver a predetermined dosage of material, for example, to the mouth of a patient, then manipulate the material with fibers 206 and cushioning material 204. Optionally, the delivery system can be resealable for a number of different applications.

As shown, reservoir 210 comprises an elongate member having a cavity 212 in which fluid 214 is selectively placed. Cavity 212 is in fluid communication with hollow chamber 216 in main body 202. For example, cavity 212 may communicate with hollow chamber 216 in main body 202 through port 218 in main body 202, which is in fluid communication with hollow chamber 216.

A circular flange 220 coupled to main body 202 slides back and forth within cavity 212 and abuts shoulders 222 of reservoir 210 when main body 202 is moved to an extended position, as shown in FIG. 9A. An O-ring 224 prevents fluid from leaking from reservoir 210. When main body 202 is moved to a contracted position, as shown in FIG. 9B, fluid 214 compressed within reservoir 210 is expelled through channel 216 and out of elastomeric member 204 onto the surface of the elastomeric member, fibers 206 and optionally into the mouth of a patient or other object. Thus, movement of the hollow main body with respect to the reservoir selectively causes fluid within the main body to flow from the elastomeric member. This fluid can then be delivered to a desired location.

A lid 226 is selectively mounted on elastomeric member 204 and its associated fibers 206 to prevent fluid from inadvertently leaking from applicator 200. Lid 226 is an example of means for selectively sealing applicator 200.

With reference to FIGS. 10A and 10B, as another example of such means for selectively sealing an applicator, main body 202a can be rotatably mounted on a base member 230a. Base member 230a is disposed within a reservoir 212a and has a port 232a therein that selectively communicates with a proximal port 218a of main body 202a. As shown in FIG. 10B, upon moving proximal port 218a, which is in fluid communication with chamber 216a, in fluid communication with port 232a (i.e. by rotating main body 202a with respect to base member 230a) fluid can flow from cavity 212a through chamber 216a and out of elastomeric member 204a, which can be a perforated member, for example. Upon aligning ports 232a and 218a and upon compressing reservoir 212a and main body 202a, as shown in FIG. 90b, fluid flows in the direction of arrows 234a through port 232a, port 218a, channel 216a and out of member 204. O-rings 224a, 225a assist in sealing fluid within reservoir 212a until it is expelled through chamber 216a.

FIGS. 11A–18B disclose a variety of different tip members for applicators of the present invention. The elastomeric tip members are designed to be coupled to the distal end of a rigid elongate body, such as body 92. In one preferred embodiment, the tip members of FIGS. 11A–11B have fibers coupled thereto (see FIG. 11B) such as through electrostatic flocking or a variety of other manners. The groove(s) of the distal tips of FIGS. 11A–17B allow the tip members to compress as the tips are forced in between or against teeth. This both cushions the movement of a dental tool against the teeth and allows the tips to fit between teeth and into other difficult to reach places in the mouth of a patient.

The elastomeric tip members of FIGS. 11A–17B each feature an elastomeric spherical member having at least one groove therein. For example, distal tip member 110 of FIGS. 11A–11C features an elastomeric spherical member 112 and having a V-shaped groove 116 therein. In the embodiment shown, member 110 is coupled to a rigid body 114 (shown in a cutaway view). In light of groove 116, spherical member 112 is more likely to flex as spherical member 112 is moved against or between teeth. FIG. 11B shows an example of a fiber-covered tip member 110, which may be flocked via electrostatic flocking, for example. Such fiber covering may be employed on the other tips disclosed in FIGS. 11A–18B.

Distal tip member 120 of FIGS. 12A–12B features an elastomeric spherical member 122 having a star-shaped groove 126 therein. In the embodiment shown, member 120 is coupled to a rigid body 124 (shown in a cutaway view). In light of groove 126, spherical member 122 is more likely to flex as spherical member 122 is moved against or between teeth. The star shape allows five different portions of the tip 120 to move inwardly with respect to each other, providing flexibility in a variety of different directions.

Distal tip member 130 of FIGS. 13A–13B features an elastomeric spherical member 132 having a slot-shaped groove 136 therein. In the embodiment shown, member 130 is coupled to a rigid body 134 (shown in a cutaway view). In light of groove 136, spherical member 132 is more likely to flex as spherical member 132 is moved against or between teeth. The groove allows the different sides of the tip 130 to flex with respect to each other.

Distal tip member 140 of FIGS. 14A–14B features an elastomeric spherical member 142 having a V-shaped groove 146 therein. In the embodiment shown, member 140 is coupled to a rigid body 144 (shown in a cutaway view). In light of groove 146, spherical member 142 is more likely to flex as spherical member 142 is moved against or between teeth. The V-shaped groove allows a wide gap such that the sides of the tip can flex significantly with respect to each other.

Distal tip member 150 of FIGS. 15A–15B features an elastomeric spherical member 152 having a plurality of V-shaped grooves 156a, 156b, 156c therein. In the embodiment shown, member 150 is coupled to a rigid body 154 (shown in a cutaway view). In light of grooves 156a–c, spherical member 152 is more likely to flex as spherical member 152 is moved against or between teeth. In light of the plurality of V-shaped grooves, spherical member 152 flexes significantly when moved between teeth.

Figure 16A:
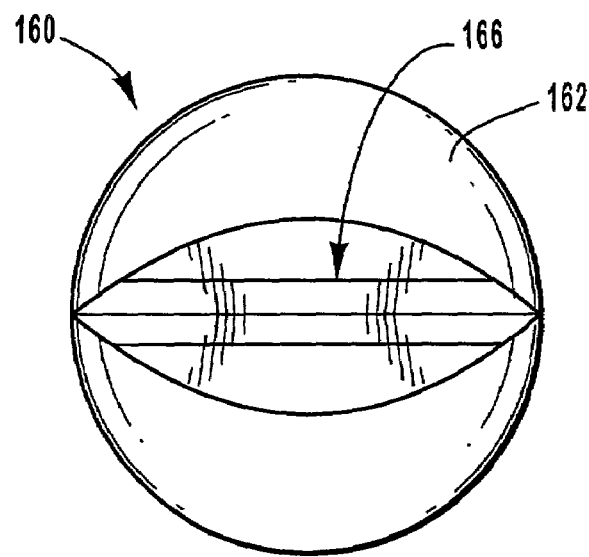
FIGS. 16A–16B demonstrate an alternate cushioned applicator tip member of the present invention having a spherical configuration with a groove therein.
Figure 16B:
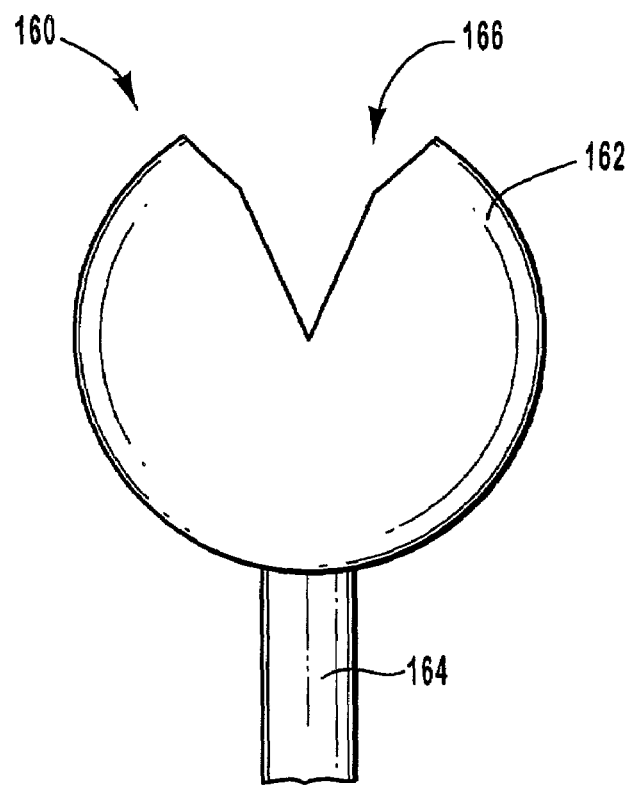

Distal tip member 160 of FIGS. 16A–16B features an elastomeric spherical member 162 having a modified V-shaped groove 166 therein. In the embodiment shown, member 160 is coupled to a rigid body 164 (shown in a cutaway view). In light of groove 166, spherical member 162 is more likely to flex as spherical member 162 is moved against or between teeth.

Figure 17A:
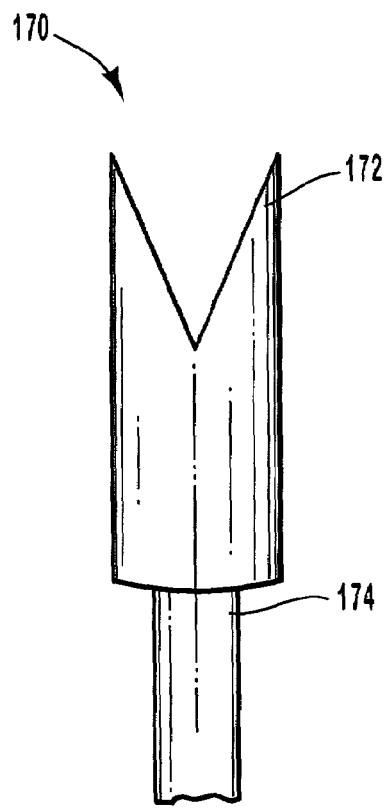
FIGS. 17A–17B demonstrate an alternate cushioned applicator tip member of the present invention having a V-shaped groove therein.
Figure 17B:
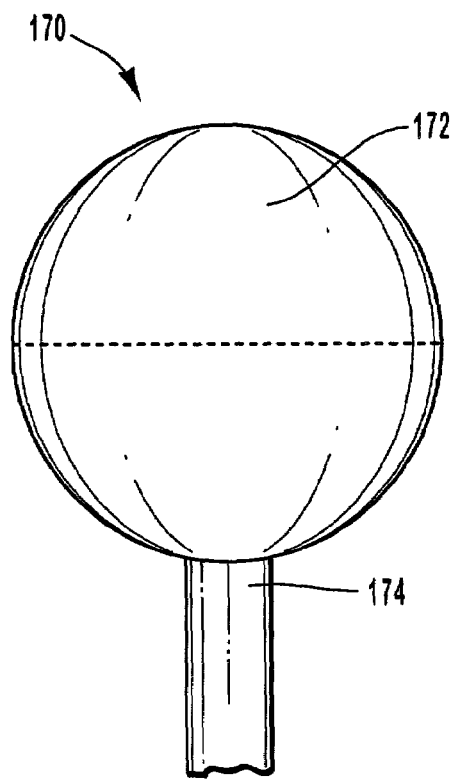

FIGS. 17–18 disclose different paddle tip members of the present invention. Distal tip member 170 of FIGS. 17A–17B features an elastomeric paddle shaped member 172 having a V-shaped groove therein. Member 170 is coupled to body 174. In light of the V-shaped groove, paddle shaped member 172 is more likely to flex as the paddle-shaped member 172 is moved against or between teeth.

Figure 18A:
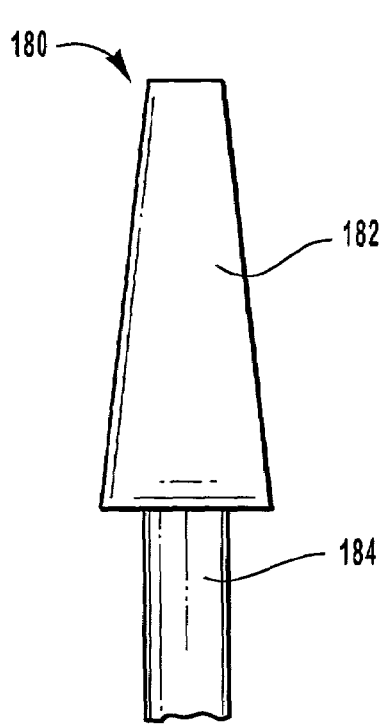
FIGS. 18A–18B demonstrate an alternate cushioned applicator tip member of the present invention having a paddle shaped configuration.
Figure 18B:
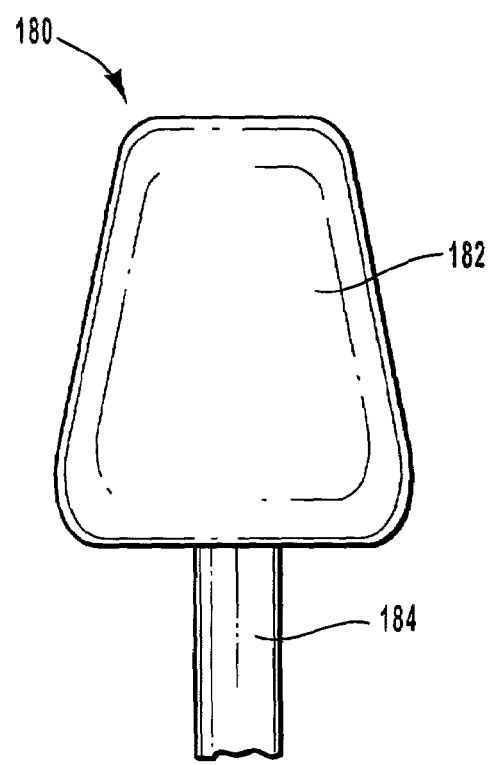

FIGS. 18A–18B also disclose a paddle tip member of the present invention. Distal tip 180 of FIGS. 18A–18B features an elastomeric paddle shaped member 182 coupled to a rigid body 184. This paddle shape provides convenient manipulation of material to be delivered to a desired location.

FIGS. 19–30 demonstrate examples of non-slip gripping surfaces that can be employed in the present invention to provide a non-slip grip along the rigid body of the applicators of the present invention, such as the applicators shown in FIGS. 3A–8B. FIG. 31 demonstrates a perspective view of one example of the location of a non-slip material with respect to the remainder of the rigid body of the applicator 186 of FIG. 19, although a variety of different applicator configurations are also possible. Applicator 186 of FIG. 31 has an elastomeric, spherically shaped distal tip member 188, coupled to body 186.

The non-slip material employed in such non-slip grips can comprise the same elastomeric material as described as being coupled to the distal end of the elongate body. The non-slip portion may, for example, comprise a polyurethane, rubber, a thermoplastic elastomer, or another deformable material disclosed herein, such as any of those materials disclosed for use as an elastomeric member coupled to the distal end of an elongate body. Optionally, however, a different material is employed for the non-slip portion. As shown, the rigid body of the dental tool of the present invention may have a variety of different gripping surfaces.

Figure 19:
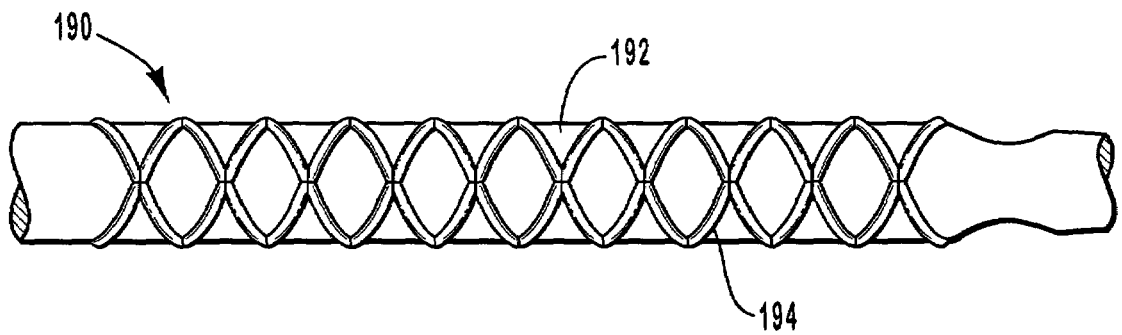
FIGS. 19–30 show various non-slip gripping portions of main bodies of applicators of the present invention.

FIG. 19 demonstrates a grip portion of the body of a dental applicator. Grip 190 comprises: (i) a grip body 192; and (ii) a network of interlocking ridges 194 extending about body 192. Ridges 194 may comprise a material that is elastomeric, for example, while body 192 is rigid, thereby providing a nonslip gripping surface. Ridges 194 are an example of means for enhancing the gripping surface of grip 190.

Figure 20:
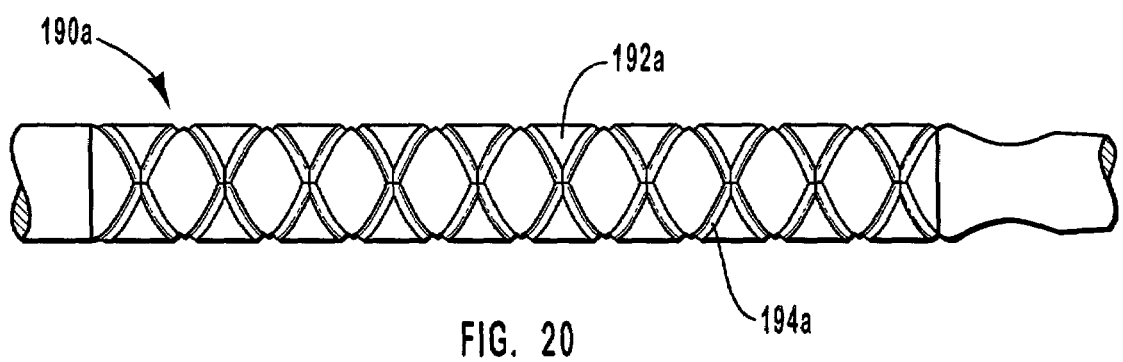

FIG. 20 demonstrates a grip portion of the body of a dental applicator. Grip 190a comprises: (i) a series of elastomeric grip body portions 192a; and (ii) a network of rigid interlocking grooves 194a dividing the grip body portions 192a. Grooves 194a and portions 192a are an example of means for enhancing the gripping surface of grip 190a.

Figure 21:
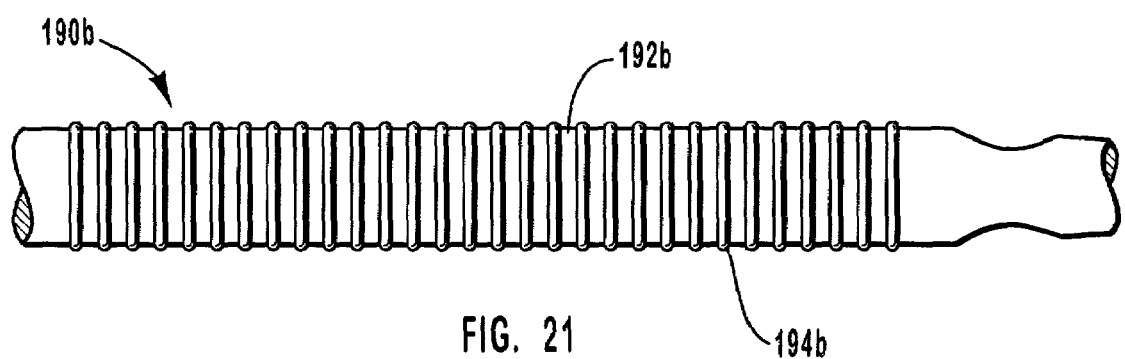

FIG. 21 demonstrates a grip portion of the rigid body of a dental applicator. Grip 190b comprises: (i) a grip body 192b; and (ii) a series of ridges 194b extending about body 192b. Ridges 194b may comprise a material that is elastomeric, for example, while body 92b is rigid, thereby providing a nonslip gripping surface. Ridges 194b are an example of means for enhancing the gripping surface of grip 190b.

Figure 22:
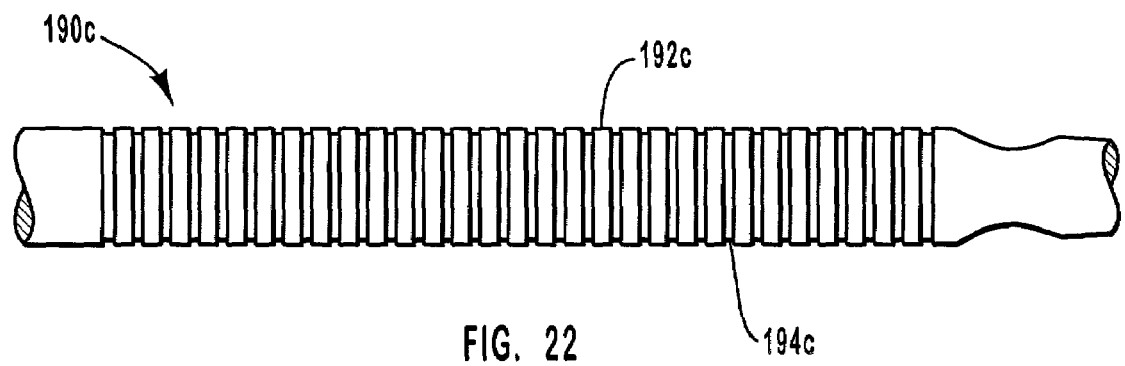

FIG. 22 demonstrates a grip portion of the rigid body of a dental applicator. Grip 190c comprises: (i) a series of elastomeric grip body portions 192c; and (ii) a series of grooves 194c extending about body 192c. Grooves 194c and grip body portions 192c are an example of means for enhancing the gripping surface of grip 190c.

Figure 23:
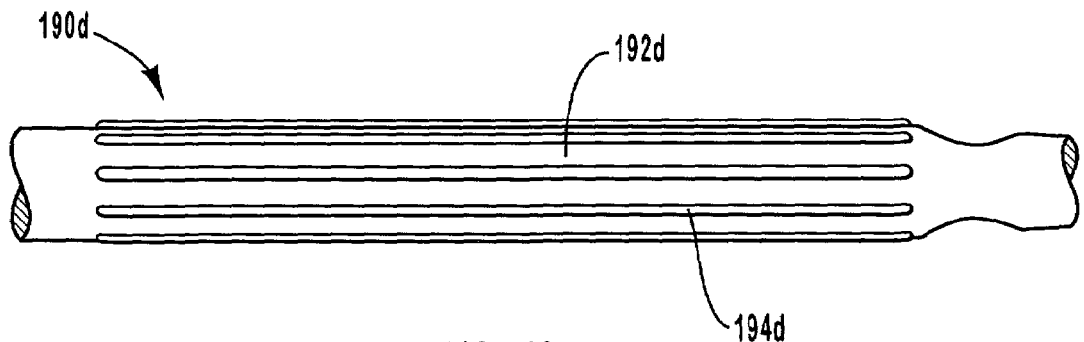

FIG. 23 demonstrates a grip portion of the rigid body of a dental applicator. Grip 190d comprises: (i) a grip body 192d; and (ii) a series of longitudinal ridges 194d extending about body 192d. Ridges 194d may comprise a material that is elastomeric, for example, while body 192d is rigid, thereby providing a nonslip gripping surface. Ridges 194d are an example of means for enhancing the gripping surface of grip 190d.

Figure 24:
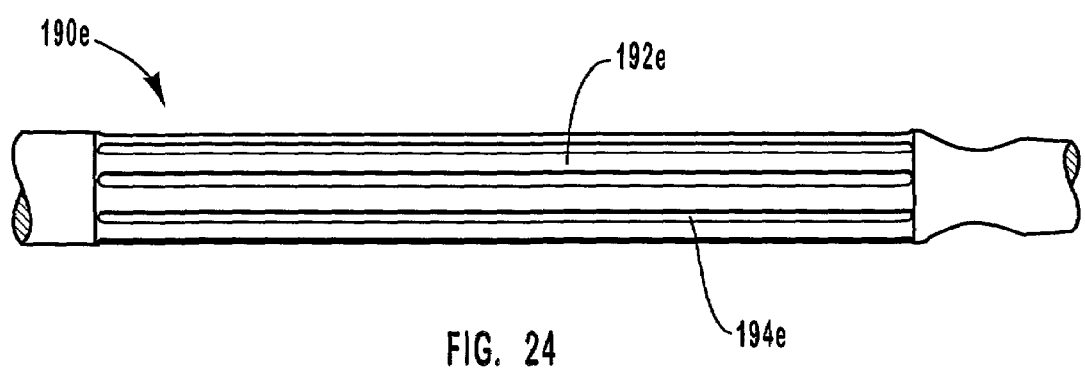

FIG. 24 demonstrates a grip portion of the rigid body of a dental applicator. Grip 190e comprises: (i) a series of elastomeric grip body portions 192e; and (ii) a series of rigid longitudinal grooves 194e extending adjacent body portions 192e. Grooves 194e and body portions 192e are an example of means for enhancing the gripping surface of grip 190e.

Figure 25:
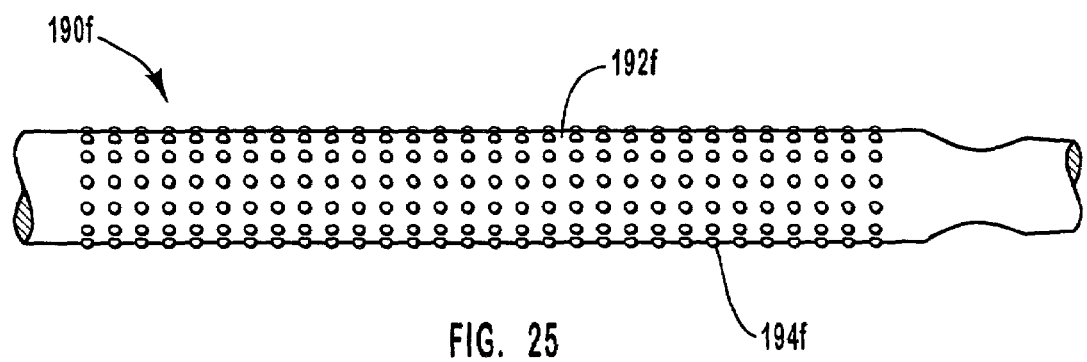

FIG. 25 demonstrates a grip portion of the rigid body of a dental applicator. Grip 190f comprises: (i) a grip body 192f; and (ii) a series of knobs 194f extending about body 192f. Knobs 194f may comprise a material that is elastomeric, for example, while body 192f is rigid, thereby providing a nonslip gripping surface. Knobs 1 94f are an example of means for enhancing the gripping surface of grip 190f.

Figure 26:
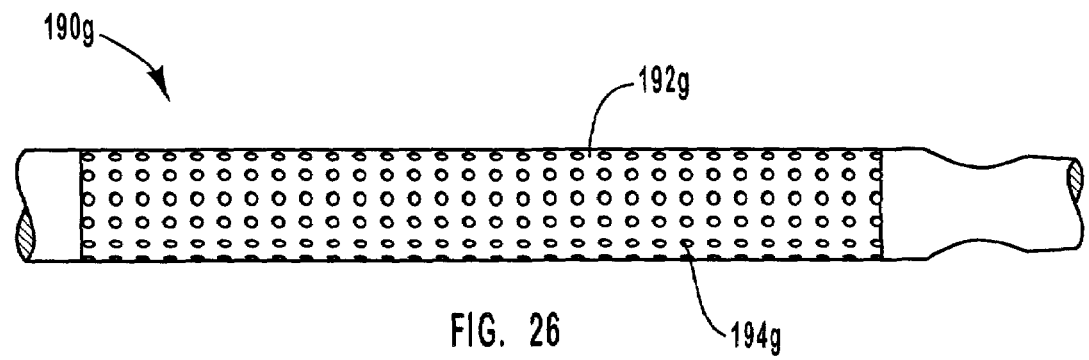

FIG. 26 demonstrates a grip portion of the rigid body of a dental applicator. Grip 190g comprises: (i) an elastomeric grip body portion 192g; and (ii) a series of rigid grooves 194g in body portion 192g. Grooves 194g and body portion 192g are an example of means for enhancing the gripping surface of grip 190g.

Figure 27:
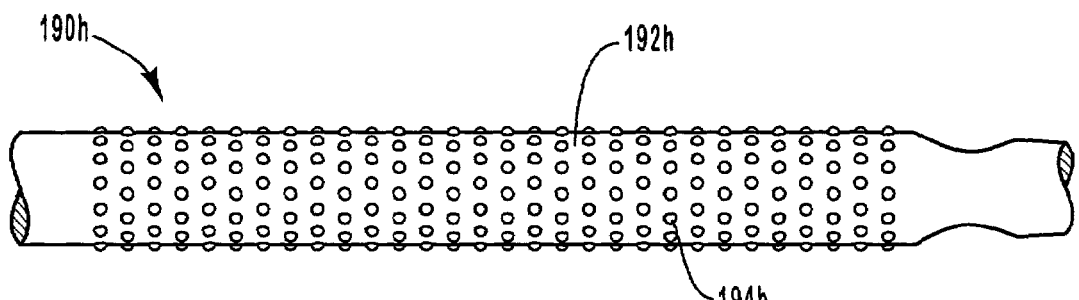

FIG. 27 demonstrates a grip portion of the rigid body of a dental applicator. Grip 190h comprises: (i) a grip body 192h; and (ii) a series of knobs 194h extending about body 192h. Knobs 194h may comprise a material that is rigid for example, while body 192h is elastomeric, thereby providing a nonslip gripping surface. Knobs 194h and body 192h are an example of means for enhancing the gripping surface of grip 190h.

Figure 28:
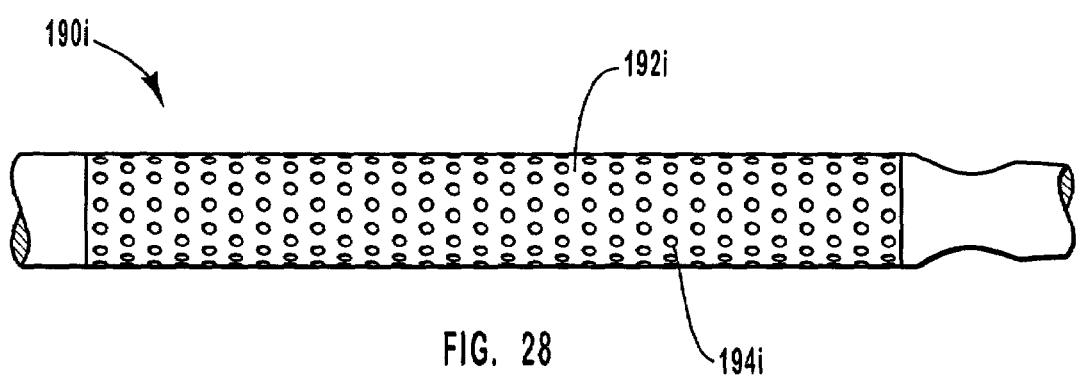

FIG. 28 demonstrates a grip portion of the rigid body of a dental applicator. Grip 190i comprises: (i) an elastomeric grip body portion 192i; and (ii) a series of elastomeric grooves 194i in body portion 192g. Grooves 194g and body portion 192g are an example of means for enhancing the gripping surface of grip 190g.

Figure 29:
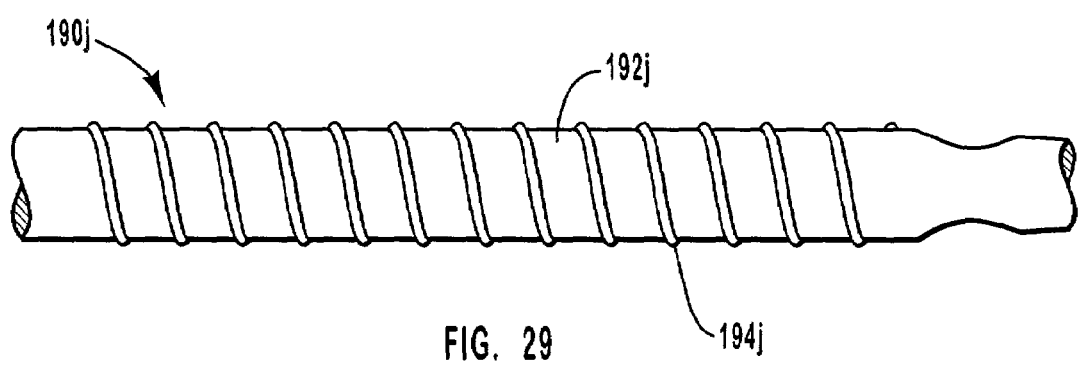

FIG. 29 demonstrates a grip portion of the rigid body of a dental applicator. Grip 190j comprises: (i) a grip body 192j; and (ii) a winding ridge 194j extending about body 192j. Ridge 194j may comprise a material that is elastomeric, for example, while body 192j is rigid, thereby providing a nonslip gripping surface. Ridges 194j are an example of means for enhancing the gripping surface of grip 190j.

Figure 30:
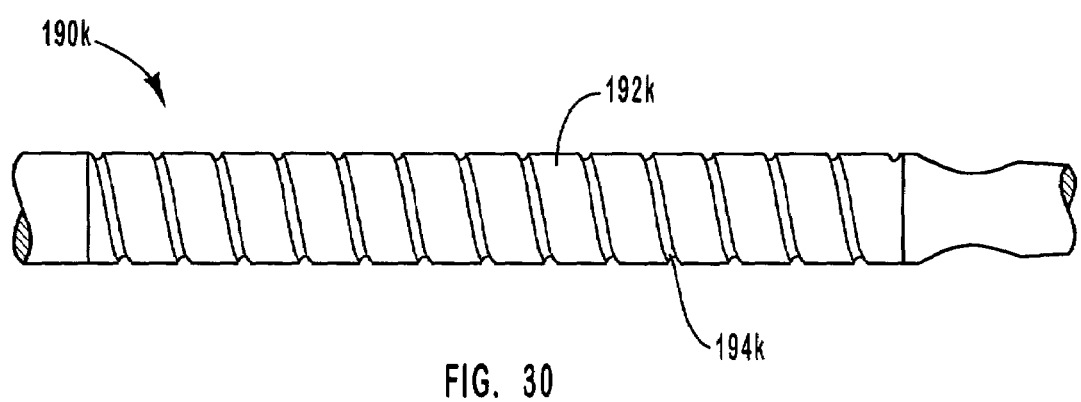
Figure 31:
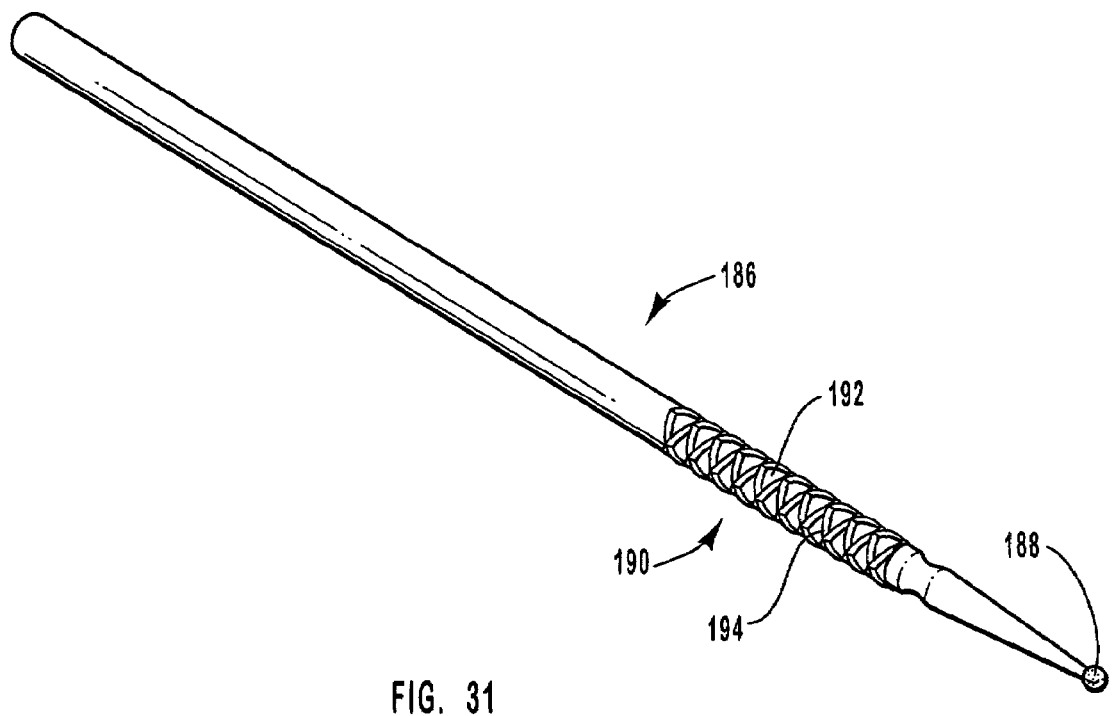
FIG. 31 is a perspective view of the body of the applicator featured in FIG. 19 and having an elastomeric, spherically shaped distal tip member coupled to a rigid body member.

FIG. 30 demonstrates a grip portion of the rigid body of a dental applicator. Grip 190*k* comprises: (i) a series of elastomeric grip body portions 192*k*; and (ii) a winding groove 194*k* extending about body 192*k*. Groove 194*k* and grip body portions 192*k* are an example of means for enhancing the gripping surface of grip 190*k*.

The dental instruments of the present invention may be used to apply various dental materials into the mouth of a patient. One method for delivering a dental material within the mouth of a patient comprises: (1) providing a dental instrument, comprising: (A) a main body having a proximal end and a distal end; and (B) means for cushioning the distal end of the main body; (2) loading the dental instrument with a dental material; and (3) delivering the dental material within the mouth of the patient (possibly including, for example, moving the distal delivery end of the dental instrument into the mouth of the patient and depressing a plunger or scraping material from the instrument against the teeth or gums). The dental instrument may comprise, for example, (i) a delivery system comprising a delivery tip and a delivery device coupled thereto; or (ii) an applicator.

For example, in one embodiment, the dental instrument comprises a delivery tip having a syringe or another delivery device coupled thereto, the delivery tip having an elastomeric member on a distal end thereof. In such an embodiment, delivering the dental material within the mouth of a patient may comprise depressing a plunger movably coupled to a barrel of the syringe. Loading the dental instrument may comprise placing a dental material within a barrel of the syringe, for example.

In another embodiment, the instrument comprises a dental applicator and loading the instrument with a dental material comprises: (i) placing a dental material on the applicator, e.g., specifically on the elastomeric cushioning member (such as by scooping a quantity of dental material onto a dental applicator); or (ii) loading a reservoir such as reservoir 210 or 210*a* with a dental material.

In one embodiment, the method of use further comprises positioning the dental instrument within the patient's mouth against air bubbles within the mouth of the patient, such as by positioning the fibers of the instrument against air bubbles within the mouth of the patient.

Thus, a method for furthering a dental procedure without causing pain to the teeth or gums of a patient, comprises: (1) providing (i) a rigid main body having a proximal end and a distal end, the rigid main body being configured to be grasped by a practitioner; and (ii) means for cushioning the distal end of the rigid main body; and (2) positioning at least a portion of the dental instrument within the patient's mouth. In one embodiment, the dental instrument comprises an instrument selected from the group consisting of: (i) an applicator; and (ii) a syringe. One embodiment of the method further comprises: (i) delivering a material into the mouth of the patient; and (ii) placing the instrument against the material delivered. Placing the delivery tip against the material delivered may comprise placing a portion of the instrument (e.g., the fibrous portion) against air bubbles within the material delivered in order to eliminate the air bubbles.

Thus, one embodiment of a method for positioning a dental instrument within the mouth of a patient so as to remove air bubbles from material delivered within the mouth of the patient is conducted without injuring or causing pain to the teeth or gums of the patient. Such a method, as described herein may comprise providing a dental applicator or delivery tip having a plurality of fibers at a distal end thereof as described herein and positioning the dental applicator within the patient's mouth against air bubbles within the mouth of the patient, such that the fibers contact and burst the air bubbles.

Figure 32:
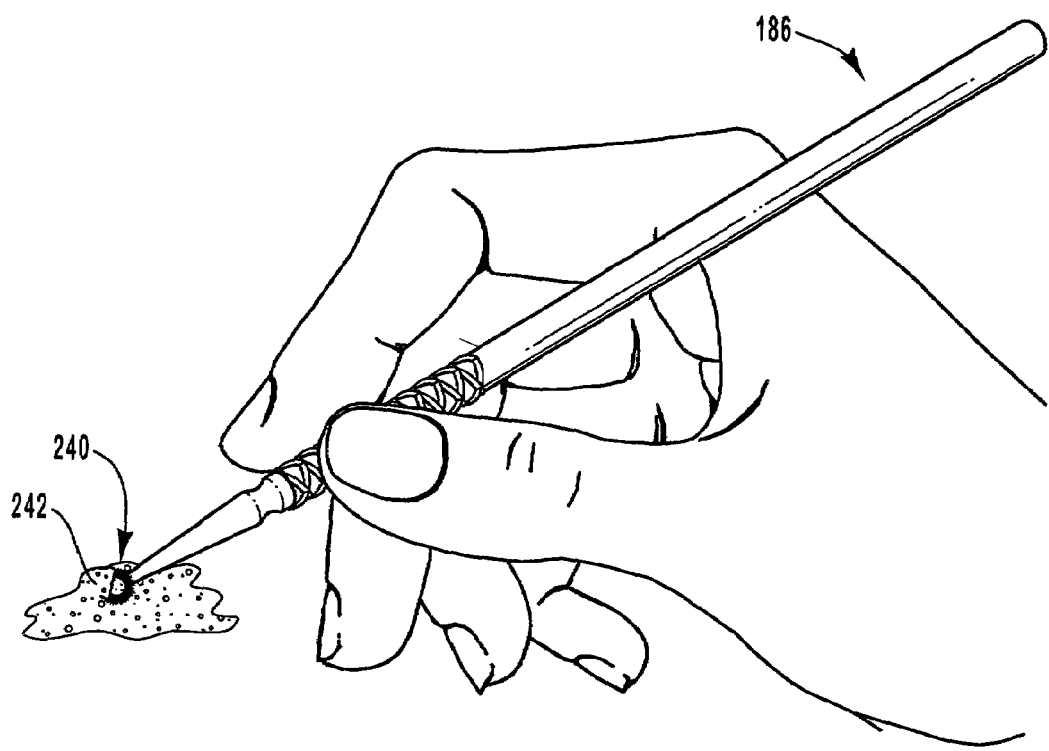
FIG. 32 is a perspective view of the applicator shown in FIG. 31 with a dental material placed thereon.
Figure 33:
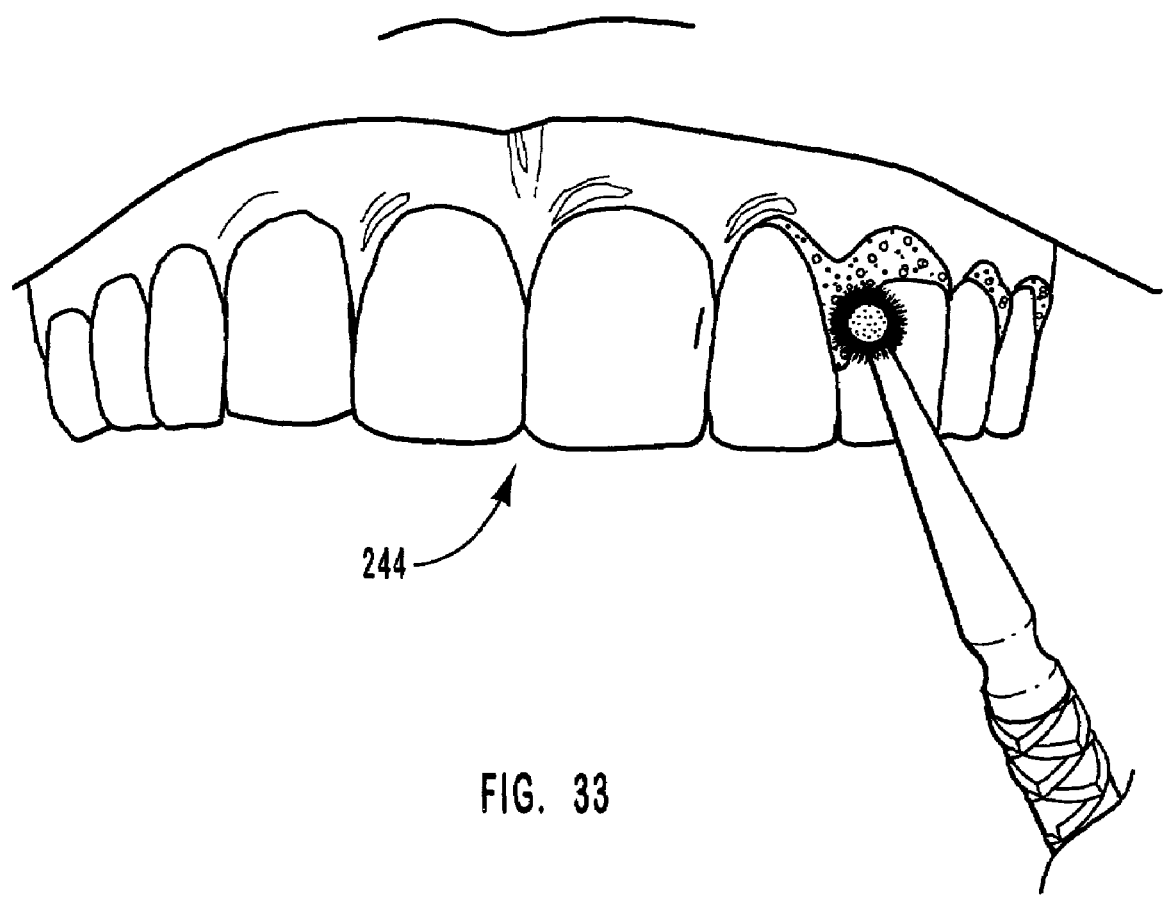
FIG. 33 is a view of the applicator of FIG. 31 moved within the mouth of a patient such that fibers on the applicator contact and eliminate air bubbles within a delivered material.

FIGS. 32–33 demonstrate an example of applicator 186 having fibers 240 coupled to elastomeric member 188 and having a dental material 242 placed thereon. Upon placing the cushioned, fiber-covered portion of applicator 186 into the mouth 244 of a patient, the material 242 can be delivered to a desired location. FIG. 33 shows a mouth 244 in which the material 242 has been delivered against the teeth and gums of a patient. As depicted, the material 242 can be delivered to a desired location, after which the fibers 240 can be moved against air bubbles 246 formed in the material to eliminate the air bubbles.

Figure 11A:
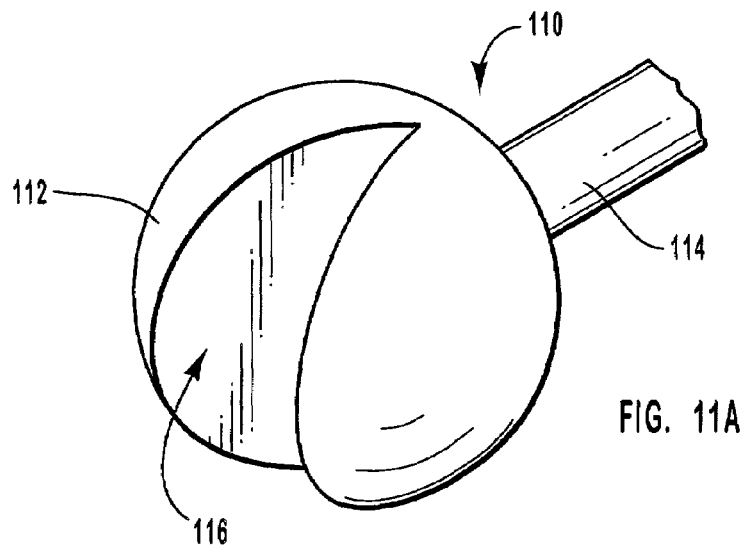
FIGS. 11A–11C demonstrate a cushioned applicator tip member of the present invention having a spherical configuration with a groove therein, with flocking shown on the tip in the view of FIG. 11B.
Figure 11B:
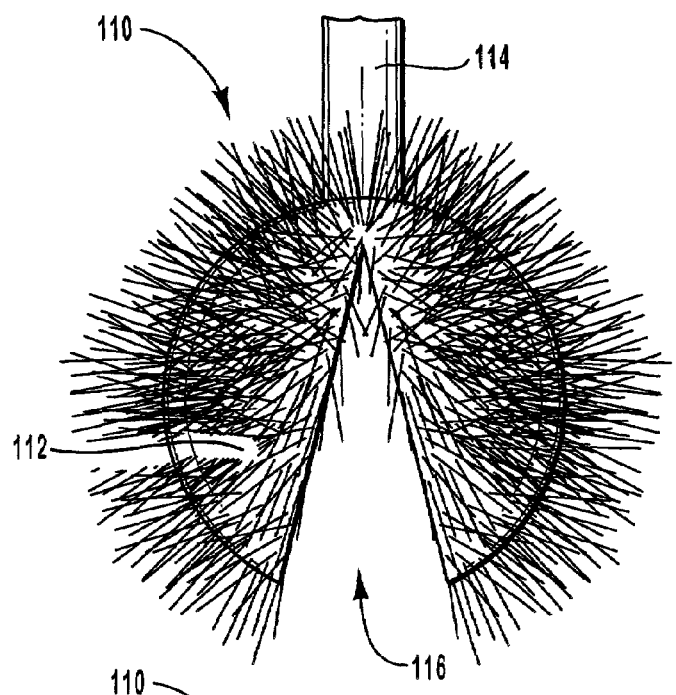
Figure 11C:
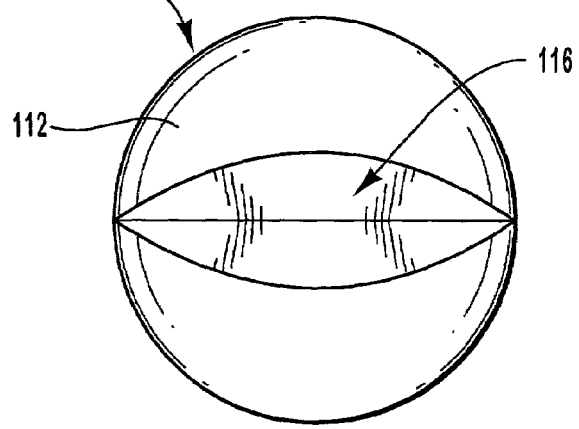

The fibers of the present invention may be coupled to the elastomeric material in a variety of different patterns. For example, the fibers may substantially surround a hollow elastomeric member 17 or a rigid tubular body 36 or may be placed thereon in discrete clumps, for example. Similarly, the fibers may substantially surround a tip, such as shown in FIGS. 11B and 32, or may only be mounted on one or more sides or surfaces thereof, depending upon a desired application.

According to the present invention, various dental instruments can be manufactured through the methods described above, including the use of flocking, such as electrostatic flocking, for example. Such instruments may comprise elastomeric portions to which fibers are flocked, for example. Examples of dental instruments that can be manufactured using the methods described above, including the use of flocking, such as electrostatic flocking, include the instruments disclosed in the U.S. applications entitled "Tongue Brush", U.S. patent application Ser. No. 09/484,302, filed Jan. 18, 2000, which is incorporated herein by reference and "Tongue Cleaning Device and Related Methods, U.S. patent application Ser. No. 09/511,827, filed Feb. 24, 2000, which is also incorporated herein by reference. The dental instruments disclosed in these U.S. patent applications can be formed through the use of a method comprising electrostatic flocking, rather than employing integral fibers, for example.

Nevertheless, while the applicators and delivery tips described herein are particularly useful in the field of dentistry, it is also possible to use such applicators and delivery tips or similar applicators and tips in a variety of different fields, including the fields of painting, nail polish, make up, and other fields in which a liquid or pliable material is delivered to a surface and/or manipulated on a surface.

Aspects of the present invention are also disclosed in the patent applications to Fischer et al filed on Oct. 30, 2000 entitled "Cushioned, Fiber-Covered Dental Applicators," and "Methods for Delivering Dental Compositions Within the Mouth of a Patient Using a Cushioned Dental Instrument", which are each incorporated herein by reference.

Figure 34A:
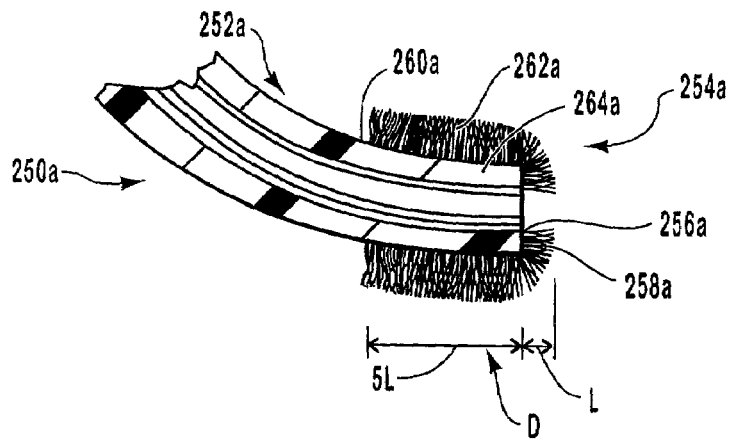
FIG. 34A is a cross sectional, cutaway side view of a fibrous delivery tip of the present invention. A portion of the fibers extend a length "L" distally beyond the rim of the hollow body and a portion of the fibers are coupled along the wall a distance "D" proximally with respect to the rim. The distance "D" is about five times greater than the length "L".
Figure 34B:
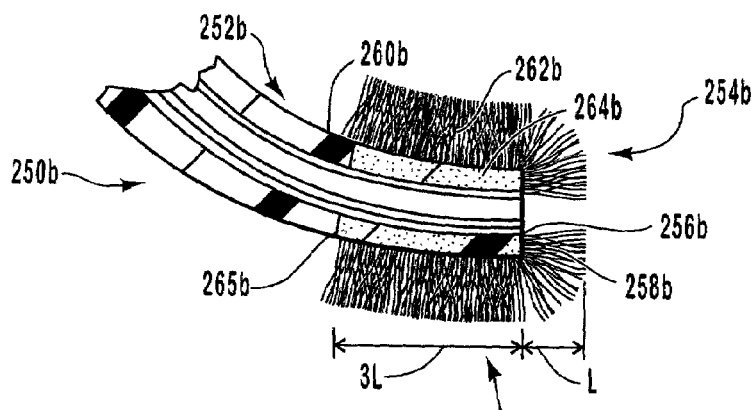
FIG. 34B is another cross sectional, cutaway side view of a fibrous delivery tip of the present invention. A portion of the fibers extend a length "L" distally beyond the rim of the hollow body and a portion of the fibers are coupled along the wall a distance "D" proximally with respect to the rim. The distance "D" is about three times greater than the length "L".
Figure 34C:
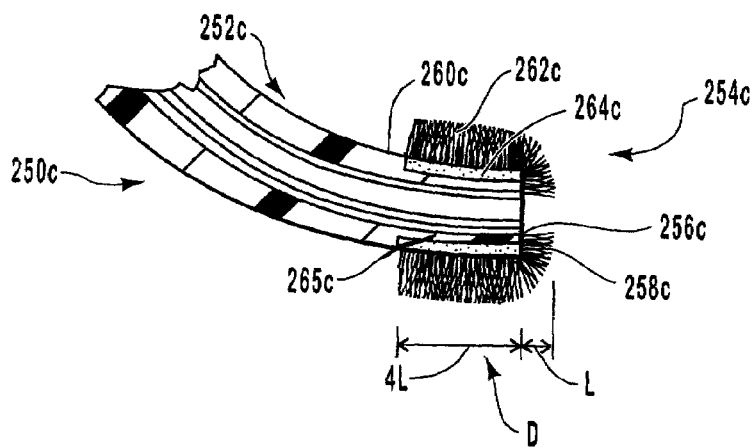
FIG. 34C is another cross sectional, cutaway side view of a fibrous delivery tip of the present invention. A portion of the fibers extend a length "L" distally beyond the rim of the hollow body and a portion of the fibers are coupled along the wall a distance "D" proximally with respect to the rim. The distance "D" is about four times greater than the length "L".

As featured in FIGS. 34A–34C and 35, and as discussed above, the present invention also relates to a dental delivery instrument with which it is convenient to deliver a composition to the interior walls of a cavity or root canal or another wall of a dental surface. Employing the tool, which may be a delivery tip, for example, the interior walls of a dental preparation may be conveniently brushed or cleaned during a procedure in which a dental composition is delivered using the dental delivery tool. Examples of such an instrument include delivery tips 250*a*, 250*b*, and 250*c* shown in respective FIGS. 34A–C in a cutaway view. The hollow, elongate distal delivery ends 252*a*–*c* of respective delivery tips are shown in FIGS. 34A–C. Each of these may comprise the distal delivery end of a delivery tip, such as tips 10, 20 and/or 30 shown in respective FIGS. 1A, 1B and 1C. For example, delivery tip 250a is shown in a perspective view in FIG. 35.

Figure 35:
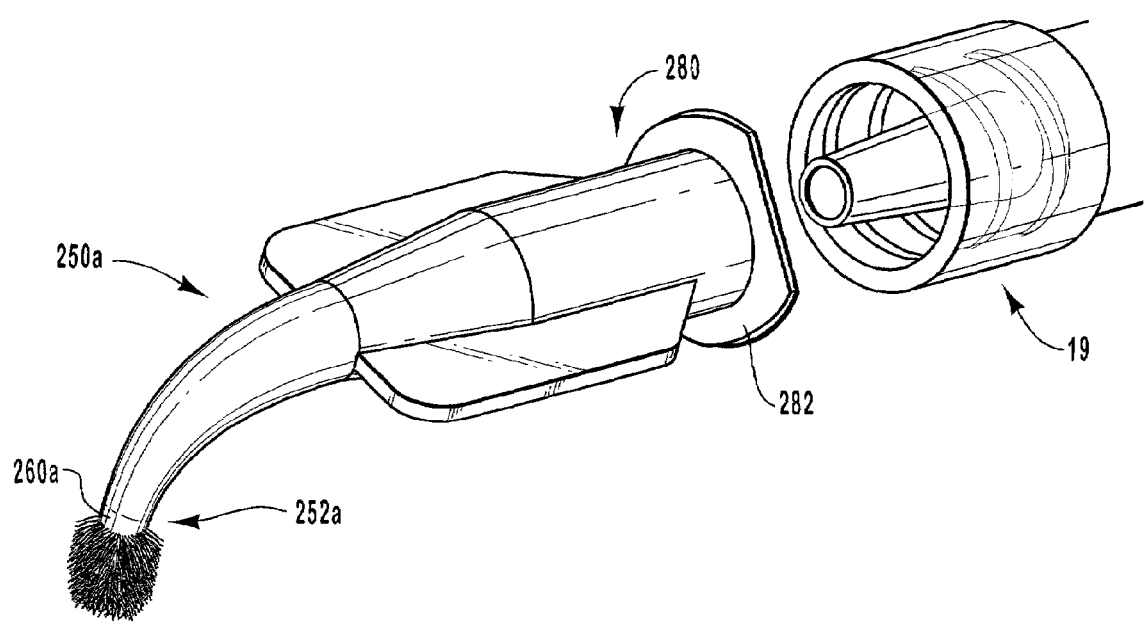
FIG. 35 is an example of a dental tool comprising the hollow delivery tip featured in cross section in FIG. 34A and a syringe configured to deliver a dental composition to the delivery tip.

With specific reference now to FIGS. 34a and 35, delivery tip 250a comprises an elongate, tubular, hollow body 280 having a hollow proximal receiving end 282 and a hollow distal delivery end 252a. Tubular body 280 has a passageway extending from an inlet orifice at proximal end 282 to an outlet orifice at the tubular distal end 252a through which a dental composition may flow. A distal rim 256a is located at the orifice of the distal end 252a. Tubular body 280 may have a variety of different configurations such as elongate, curved, straight, or irregular configurations or a variety of other configurations known to those skilled in the art.

Tip 250a further comprises a plurality of fibers 254a coupled to distal delivery end 252a, such as through electrostatic flocking. Fibers 254 can be employed to remove particles from the mouth of the patient, to remove bubbles from an impression material or other material, to manipulate, massage, or clean appliances, teeth, gums, or other portions of the mouth, as a brush, or for a variety of other purposes. These functions may occur before, after, or during delivery of material through tip 280. Fibers 254a can have a variety of different lengths. In one embodiment, short and long fibers exist in a particular bundle of fibers such that the long fibers are supported by the shorter fibers. The configuration of fibers 254a will be discussed in additional detail below.

Delivery tip 280 is configured to be coupled to a delivery device, such as a syringe 19 and to direct material delivered from syringe 19 to a desired location within the mouth of a patient. External thread 282 is an example of a means for coupling tubular body 280 to a delivery device. Through the use of thread 282, tubular body 280 can be releasably coupled to a delivery device, such as syringe 19 (e.g., by being coupled to mating threads on syringe 19). However, a variety of different means for coupling tubular body 280 to a delivery device may also be employed, such as internal threads (e.g., thread 22 of FIG. 2), male or female Luer-lock type attachment members, a configuration that allows a press fit attachment, or any other suitable arrangement understood by one skilled in the art in light of the disclosure herein.

Syringe 19 may have a variety of different configurations. In one embodiment, syringe 19 comprises a reservoir means (e.g., a barrel) for holding a quantity of a dental composition for restorative or reconstructive dental procedures and a means for controlled dispensing (e.g., a plunger) of the dental composition from the reservoir means. The plunger or other means for controlled dispensing also dispenses the composition through the delivery tip in order to apply in a precise, controlled fashion the dental composition to a small area, such as a relatively small region of a tooth surface that is to be restored or reconstructed.

As mentioned, the distal delivery end of each dental delivery tip 250a, 250b, and 250c is shown in FIGS. 34A–C and has a plurality of fibers on the distal rim and on the outer wall thereof. A portion of the fibers extend a length "L" distally beyond the rim of the hollow body and a portion of the fibers are coupled along the wall a distance "D" proximally with respect to the rim.

As a major advantage, the distance "D" is at least about two and one half times greater than the length "L". That is D=at least about 2.5L. This greatly enhances the brushing and/or cleaning effect of the fibers and makes it more convenient to brush or clean internal walls of dental preparations before, after, or during delivery of a dental composition through the passageway of the delivery device.

For example, the distal delivery end 252a–c of each hollow body has a plurality of respective fibers 254a–c coupled to a respective distal rim 256a–c and the exterior surface of a respective circular wall 260a–c. The passageway extending through body 280 is defined by the interior surface of the circular wall 260a. Fibers 254a thus comprise (i) rim fibers 258a–c which are coupled to rim 254a; and (ii) wall fibers 262a–c which are coupled to a respective body wall 260a–c. The wall fibers 262a–c each collectively form a respective fiber bundle.

In one embodiment, the rim fibers 258a–c extend substantially perpendicularly from the face 256a–c of a respective rim 256a–c and the body fibers 262a–c extend substantially perpendicularly from a respective circular wall 260a–c.

As shown, a portion of the fibers 254a–c extend a length "L" distally beyond the rim of each respective hollow body. Furthermore, as mentioned, a portion (i.e., the wall fibers 262a–c) of the fibers are coupled along a respective wall 260a–c a distance "D" proximally with respect to a respective rim 256a–c.

In one embodiment, the fibers 254a–c extending a length "L" distally beyond each respective rim comprise rim fibers 258a–c that are coupled to respective rims 256a–c. However, the fibers 254a–c extending a length "L" distally beyond the rim of each respective hollow body may also comprise the free ends of wall fibers 262a–c that bend sufficiently such that they extend distally beyond a respective rim. Thus, it is possible that some fibers that actually extend distally beyond the rim are also coupled to the wall, yet bend sufficiently so as to extend distally beyond the rim.

Advantageously, the distance "D" is at least about two and one half times greater than the length "L" in each of the embodiments of FIGS. 34A–34C. For example, as shown in FIG. 34A, the distance "D" that the fiber bundle 262a comprising wall fibers 262a extends along wall 260a is approximately 5 times the length "L" of the fibers that extend distally beyond the rim 256a of tip 250a. Similarly, as shown in FIG. 34B, the distance "D" that the fiber bundle 262b comprising wall fibers 262b extends along wall 264b is approximately 3 times the length "L" of the fibers that extend distally beyond rim 256b. Furthermore, as shown in FIG. 34C, the distance "D" that the fiber bundle 262c comprising wall fibers 262c extends is approximately 4 times the length of "L" of the fibers that extend distally beyond rim 256c.

This dynamic is also featured in FIG. 1B, in which fibers extending from the rim of tip 10 have a length and wherein the distance that adjacent wall coupled fibers extend along the exterior wall is at least about 2.5 times the length. Similarly, this dynamic is featured in FIG. 2B, in which fibers extending from the distal rim 39b have a length and wherein the distance that adjacent wall coupled fibers extend along the respective exterior wall is at least about 2.5 times the length.

Thus, in one embodiment of the present invention, a portion of the fibers extend a length "L" distally beyond the rim of the hollow body, a portion of the fibers are coupled along the wall a distance "D" proximally with respect to the rim; and the distance "D" is at least about two and one half times greater than the length "L". Examples of such distances "D" that may be employed in the present invention include 2.5L, preferably 3L, more preferably 4L, more preferably 5L, and any fraction thereof. The distance "D"

may also be 6L, 7L, 8L, 9L, or 10L and so on up to about 20L or any fraction thereof, or even greater, depending upon a desired application.

As shown in FIG. 34A, distal delivery end 252a may comprise a rigid integral body 264a. Optionally, as shown in FIG. 34B, distal delivery end 252b may comprise a rigid body 265b having a cushioned end portion 264b coupled thereto, such as discussed above. Optionally, as shown in FIG. 34C, distal delivery end 252c may comprise a layer of elastomeric material 264c disposed about a rigid distal delivery end portion 265c, such as discussed above with reference to FIG. 2.

The delivery tips shown in FIGS. 1B, 2B, and 34A–C have a variety of different advantages. For example, by having fibers extend far along the length of the distal delivery ends 252a–c, it is possible to readily deliver and brush a dental composition both at the most remote point within a formed tooth cavity and along the interior walls of the cavity.

Such brushing can occur by delivering a quantity of material through hollow tip 250a, then brushing the fibers against the bottom of a cavity and the interior walls thereof, for example. Optionally, the brushing can occur by delivering a quantity of material to a surface, brushing the surface with rim fibers 258a–c, then continuing the brushing with wall fibers 262a–c, thereby continuing the brushing process to smoothen and more even apply the material.

The distal delivery ends shown in FIGS. 34A–C and 35 may also be formed as a substantially straight end (or a delivery end having a different curvature) and may be part of an endodontic irrigator, or applicator for example. Thus, the delivery tools of the present invention may comprise dental delivery tips, dental applicators or endodontic irrigators, for example.

The fibers of FIGS. 34A–C may be coupled to the hollow body of the dental delivery instrument through a variety of different methods, such as those previously discussed herein, such as electrostatic flocking. Any other fibers suitable for electrostatic flocking may also be employed. Similarly, the materials used for body 280 and/or the adhesive to adhere the fibers to body 280 may comprise those materials described above. The fibers of FIGS. 34A–C may also have a variety of different lengths and diameters, such as those discussed previously with respect to delivery tips and/or applicators.

In one embodiment, the length of the fibers of the delivery tips disclosed herein is in the range from about 0.2 mm to about 5 mm, preferably about 0.3 mm to about 3 mm, and more preferably from about 0.4 mm to about 2 mm. In this embodiment, the diameter of the fibers of the delivery tips may be in the range from about 1 Denier to about 15 Denier, and more preferably in the range from about 1.5 Denier to about 10 Denier, for example. This embodiment may be useful for delivering sealing agents, for example.

In yet another embodiment, such as when higher viscosity materials (e.g., impression materials) are employed, the length of the fibers may be in the range from about 0.3 mm to about 5 mm, preferably about 1 mm to about 3 mm, and more preferably from about 1.5 mm to about 2 mm. The diameter of such fibers may be in the range from about 3 Denier to about 75 Denier, about 3 Denier to about 45 Denier, and more preferably in the range from about 6 Denier to about 20 Denier, for example. This embodiment may be useful for removing bubbles in impression material, for example.

Also by way of example, the fiber length for the fibers of the applicators and/or irrigator tips disclosed herein may be in the range from about 0.2 mm to about 3 mm, preferably from about 0.5 mm to about 2 mm, more preferably from about 0.7 mm to about 1.5 mm, such as about 1 mm, for example. In one embodiment, the fiber diameter of the applicators is in the range from about 1 Denier to about 45 Denier, preferably about 1.5 Denier to 20 Denier, and more preferably in the range from about 1.5 Denier to about 10 Denier.

In an embodiment comprising an endodontic irrigator, a hollow distal delivery end having the fiber arrangement the same as or similar to FIGS. 34A–C may comprise a cannula that is coupled to a hub. The cannula and hub assembly may be configured as discussed in U.S. application Ser. No. 09/766,708, entitled "Endodontic Irrigator Tips Having Fiber Covered Cannulas and Related Methods," which is incorporated herein by reference. The fibers used for irrigator tips may also have the fiber lengths, diameters, and/or composition of the fibers disclosed therein. Similarly, the materials used for the cannula, hub, and adhesive for coupling the fibers to the cannula may be those described in the Ser. No. 09/766,708 application, for example.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dental delivery tool sized and configured for delivery of a dental composition into a dental preparation, comprising:
   a hollow body configured to deliver a dental composition therefrom, the hollow body having a proximal receiving end, a distal delivery end terminating with an exit orifice and a rim that surrounds the exit orifice, and a passageway communicating therebetween, the hollow body having a body wall extending between the rim at the distal delivery end and the proximal receiving end, the rim being oriented laterally relative to the body wall; and
   a plurality of fibers coupled to at least a portion of the hollow body, said fibers having first ends coupled to the hollow body and second ends extending laterally away from the hollow body;
   wherein the fibers have a length in a range of about 0.2 mm to about 5 mm and a diameter in a range of about 1 Denier to about 15 Denier;
   wherein a portion or the fibers extend a length "L" distally beyond the rim of the hollow body;
   wherein length "L" is in a range of about 0.2 mm to about 5 mm;
   wherein a portion of the fibers are coupled along the body wall a distance "D" proximally with respect to the rim; and
   wherein the distance "D" is at least about three times greater than the length "L".

2. A dental delivery tool as recited in claim 1, wherein at least a portion of the fibers extending the length "L" distally beyond the rim of the hollow body are coupled to the rim of the hollow body so as to extend laterally away from the rim.

3. A dental delivery tool as recited in claim 2, wherein at least a portion or the fibers coupled to the rim extend substantially perpendicularly from a face of the rim.

4. A dental delivery tool as recited in claim 1, wherein at least a portion of the fibers coupled along the wall of the hollow body extend substantially perpendicularly from the wall.

5. A dental delivery tool as recited in claim 1, wherein the delivery tool comprises a delivery tip.

6. A dental delivery tool as recited in claim 5, wherein the delivery tip is adapted for attachment to a syringe.

7. A dental delivery tool as recited in claim 1, wherein the delivery tool comprises an endodontic irrigator having a diameter so as to fit within a root canal of a tooth.

8. A dental delivery tool as recited in claim 1, wherein the delivery tool comprises a dental applicator.

9. A dental delivery tool as recited in claim 1, wherein at least a portion of the hollow body is curved.

10. A dental delivery tool as recited in claim 1, wherein at least a portion of the hollow body is rigid.

11. A dental delivery tool as recited in claim 1, wherein the fibers are deposited onto the hollow body by electrostatic flocking.

12. A dental delivery tool as recited in claim 1, wherein the distance "D" is at least about four times greater than the length "L".

13. A dental delivery tool as recited in claim 1, wherein the distance "D" is at least about five times greater than the length "L".

14. A dental delivery tool sized and configured for delivery of a dental composition into a dental preparation, comprising:
 a hollow body configured to deliver a dental composition therefrom, the hollow body having a proximal receiving end, a distal delivery end terminating with an exit orifice and a rim that surrounds the exit orifice, and a passageway communicating therebetween, the hollow body having a body wall extending between the rim at the distal delivery end and the proximal receiving end, the rim being oriented laterally relative to the body wall; and
 a plurality of fibers coupled to at least a portion of the hollow body, said fibers having first ends coupled to the hollow body and second ends extending laterally away from the hollow body;
 wherein the fibers have a length in a range of about 0.3 mm to about 5 mm and a diameter in a range of about 3 Denier to about 75 Denier;
 wherein a portion of the fibers extend a length "L" distally beyond the rim of the hollow body;
 wherein length "L" is in a range of about 0.3 mm to about 5 mm;
 wherein a portion of the fibers are coupled along the body wall a distance "D" proximally with respect to the rim; and
 wherein the distance "D" is at least about three times greater than the length "L".

15. A dental delivery tool as recited in claim 14, wherein at least a portion of the fibers extending the length "L" distally beyond the rim of the hollow body extend substantially perpendicularly from a face of the rim.

16. A dental delivery tool as recited in claim 14, wherein at least a portion of the fibers coupled along the wall of the hollow body extend substantially perpendicularly from the wall.

17. A dental delivery tool as recited in claim 14, further comprising coupling means for coupling the hollow body to a syringe.

18. A dental delivery tool as recited in claim 14, wherein the fibers are deposited onto the hollow body by electrostatic flocking.

19. A dental delivery tool as recited in claim 14, wherein the distance "D" is at least about four times greater than the length "L".

20. A dental delivery tool as recited in claim 14, wherein the distance "D" is at least about five times greater than the length "L".

21. A dental delivery tool as recited in claim 14, wherein the distance "D" is at least about 6 times greater than the length "L".

22. A dental delivery tool as recited in claim 14, wherein the distance "D" is at least about 7 times greater than the length "L".

23. A dental delivery tool as recited in claim 14, wherein the distance "D" is at least about 8 times greater than the length "L".

24. A dental delivery tool as recited in claim 14, wherein the distance "D" is at least about 9 times greater than the length "L".

25. A dental delivery tool as recited in claim 14, wherein the distance "D" is at least about 10 times greater than the length "L".

26. A method for manufacturing a dental delivery tool sized and configured for delivery of a dental composition to a dental preparation, the method comprising:
 providing an elongate hollow body configured for delivery of a dental composition therefrom, the elongate hollow body having a proximal receiving end, a distal delivery end terminating with an exit orifice and a rim that surrounds the exit orifice, and a passageway communicating therebetween, the hollow body having a body wall extending between the rim at the distal delivery end and the proximal receiving end, the rim being oriented laterally relative to the body wall; and
 coupling a plurality of fibers onto at least a portion of the elongate hollow body in a manner so that a portion of the fibers extend a length "L" distally beyond the rim of the hollow body and a portion of the fibers are coupled along the body wall a distance "D" proximally with respect to the rim, and so that first ends of the fibers are coupled to the hollow body and second ends of the fibers extend laterally away from the hollow body,
 wherein the fibers have a length in a range of about 0.3 mm to about 5 mm in a range of about 1 Denier to about 15 Denier;
 wherein the length "L" is in a range of about 0.3 mm to about 5 mm;
 wherein the distance "D" is at least about three times greater than the length "L".

27. A method as recited in claim 26, wherein the fibers are deposited onto the hollow body through electrostatic flocking.

28. A method as recited in claim 26, wherein the distance "D" is at least about four times greater than the length "L".

29. A method as recited in claim 26, wherein the distance "D" is at least about five times greater than the length "L".

30. A dental delivery tool as recited in claim 1, wherein the distance "D" is at least about 6 times greater than the length "L".

31. A dental delivery tool as recited in claim 1, wherein the distance "D" is at least about 7 times greater than the length "L".

32. A dental delivery tool as recited in claim 1, wherein the distance "D" is at least about 8 times greater than the length "L".

33. A dental delivery tool as recited in claim 1, wherein the distance "D" is at least about 9 times greater than the length "L".

34. A dental delivery tool as recited in claim 1, wherein the distance "D" is at least about 10 times greater than the length "L".

35. A method as recited in claim 26, wherein the distance "D" is at least about 6 times greater than the length "L".

36. A method as recited in claim 26, wherein the distance "D" is at least about 7 times greater than the length "L".

37. A method as recited in claim 26, wherein the distance "D" is at least about 8 times greater than the length "L".

38. A method as recited in claim 26, wherein the distance "D" is at least about 9 times greater than the length "L".

39. A method as recited in claim 26, wherein the distance "D" is at least about 10 times greater than the length "L".

40. A dental delivery tool sized and configured for delivery of a dental composition into a dental preparation, comprising:
   a hollow body configured to deliver a dental composition therefrom, the hollow body having a proximal receiving end, a distal delivery end terminating with an exit orifice and a rim that surrounds the exit orifice, and a passageway communicating therebetween, the hollow body having a body wall extending between the rim at the distal delivery end and the proximal receiving end, the rim being oriented laterally relative to the body wall, at least a portion of the hollow body being rigid; and
   a plurality of fibers coupled to at least a portion of the hollow body;
   wherein the fibers have a length in a range of about 0.2 mm to about 5 mm and a diameter in a range of about 1 Denier to about 15 Denier;
   wherein a portion of the fibers extend a length "L" distally beyond the rim of the hollow body;
   wherein the length "L" is in a range of about 0.2 mm to about 5 mm;
   wherein a portion of the fibers are coupled along the wall a distance "D" proximally with respect to the rim,
   wherein at least a portion of the fibers coupled along the wall of the hollow body extend substantially perpendicularly from the wall; and
   wherein the distance "D" is at least about three times greater than the length "L".

* * * * *

UNITED STATES PATENT AND TRADEMARK OFFICE
CERTIFICATE OF CORRECTION

PATENT NO.         : 7,040,893 B2
APPLICATION NO. : 10/068788
DATED                 : May 9, 2006
INVENTOR(S)       : Fischer It is certified that error appears in the above-identified patent and that said Letters Patent is hereby corrected as shown below:

Title Page
* Notice, change "177 days" to --143 days--

Drawings
Sheet 18, replace Figure 33 with the figure depicted herein below in which the air bubbles have been labeled with --246--

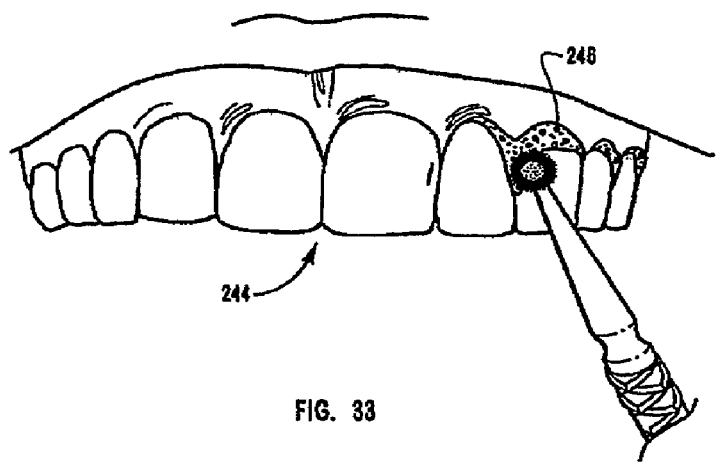

FIG. 33

Column 3
Line 51, after "elongate" remove ","

Column 6
Line 2, change "filly" to --fully--
Line 29, change "cross-sectional" to --cross sectional--

Column 11
Line 30, change "36b" to --42--

Column 13
Line 2, remove "76"

UNITED STATES PATENT AND TRADEMARK OFFICE
CERTIFICATE OF CORRECTION

PATENT NO. : 7,040,893 B2
APPLICATION NO. : 10/068788
DATED : May 9, 2006
INVENTOR(S) : Fischer It is certified that error appears in the above-identified patent and that said Letters Patent is hereby corrected as shown below:

Column 14
Line 16, change "80" to --80$a$--
Line 26, change "80" to --80$a$--

Column 16
Line 49, remove "1"

Column 17
Line 45, remove "1"

Column 18
Line 7, after "75 Denier" insert --preferably from--
Line 45, change "by" to --for--

Column 19
Line 45, change "hollow chamber" to --channel--
Line 47, change "hollow chamber" to --channel--
Line 49, change "hollow chamber" to --channel--

Column 20
Line 15, change "90$b$" to --10$b$--
Line 15, change "arrows" to --arrow--
Line 24, change "11B" to --17B--

Column 22
Line 8, change "92$b$" to --192$b$--
Line 37, change "1 94$f$" to --194$f$--
Line 57, after "body portion" change "192$g$" to --192$i$--
Line 57, after "Grooves" change "192$g$" to --192$i$--
Line 58, change "192$g$" to --192$i$--
Line 59, change "192$g$" to --192$i$--
Line 65, change "Ridges 194$j$ are" to --Ridge 194$j$ and body portion 192$j$ are--

Column 25
Line 2, change "1C" to --2--

UNITED STATES PATENT AND TRADEMARK OFFICE
CERTIFICATE OF CORRECTION

PATENT NO. : 7,040,893 B2
APPLICATION NO. : 10/068788
DATED : May 9, 2006
INVENTOR(S) : Fischer It is certified that error appears in the above-identified patent and that said Letters Patent is hereby corrected as shown below:

Column 27
Line 27, change "smoothen" to --smooth--
Line 27, change "even" to --evenly--
Line 31, after "applicator" insert --,--

Column 28
Line 52, change "or" to --of--

Signed and Sealed this

Ninth Day of January, 2007

JON W. DUDAS
*Director of the United States Patent and Trademark Office*